US 10,646,180 B2

(12) United States Patent
Davis et al.

(10) Patent No.: US 10,646,180 B2
(45) Date of Patent: May 12, 2020

(54) SYSTEM AND METHOD FOR BREAST IMAGING

(71) Applicant: General Electric Company, Schenectady, NY (US)

(72) Inventors: Cynthia Elizabeth Landberg Davis, Niskayuna, NY (US); Ying Mao, Burlingame, CA (US); Paul Langford Carson, Ann Arbor, MI (US); Oliver Daniel Kripfgans, Ann Arbor, MI (US); Jeffrey Brian Fowlkes, Ann Arbor, MI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 598 days.

(21) Appl. No.: 15/396,959

(22) Filed: Jan. 3, 2017

(65) Prior Publication Data

US 2018/0184999 A1  Jul. 5, 2018

(51) Int. Cl.
*A61B 6/00* (2006.01)
*A61B 6/04* (2006.01)
(Continued)

(52) U.S. Cl.
CPC ............ *A61B 6/502* (2013.01); *A61B 6/0414* (2013.01); *A61B 6/4417* (2013.01); *A61B 6/4435* (2013.01); *A61B 8/0825* (2013.01); *A61B 8/403* (2013.01); *A61B 8/4416* (2013.01); *A61B 6/547* (2013.01)

(58) Field of Classification Search
CPC .............................. A61B 6/502; A61B 6/4435
See application file for complete search history.

(56) References Cited

U.S. PATENT DOCUMENTS

| 6,577,703 B2 | 6/2003 | Lindstrom et al. |
| 8,565,374 B2 | 10/2013 | DeFreitas et al. |

(Continued)

FOREIGN PATENT DOCUMENTS

| DE | 199 21 100 A1 | 3/2000 |
| DE | 10 2013 219252 A1 | 3/2015 |
| JP | 2009-072410 A1 | 4/2009 |

OTHER PUBLICATIONS

Larson et al., "Automated Breast Ultrasound: Dual-Sided Compared with Single-Sided Imaging", National Center for biotechnology Information, http://www.ncbi.nlm.nih.gov/pubmed/27264914, Jun. 2, 2016. (Year: 2016).*

(Continued)

*Primary Examiner* — Alyssa M Alter
(74) *Attorney, Agent, or Firm* — Fletcher Yoder, P.C.

(57) ABSTRACT

An imaging assembly includes a compression system configured to receive and compress an object to be imaged. The compression system includes a first compression paddle and a second compression paddle. The imaging assembly further includes an ultrasound system including a first ultrasound probe coupled to the first compression paddle. The first ultrasound probe is configured to acquire a first portion of the ultrasound image information of the object. The ultrasound system also includes a second ultrasound probe coupled to the second compression paddle. The second ultrasound probe is configured to acquire a second portion of the ultrasound image information of the object.

25 Claims, 17 Drawing Sheets

(51) Int. Cl.
*A61B 8/08* (2006.01)
*A61B 8/00* (2006.01)

(56) References Cited

U.S. PATENT DOCUMENTS

| | | | |
|---|---|---|---|
| 8,853,635 | B2 | 10/2014 | O'Connor |
| 9,282,942 | B2 | 3/2016 | Mertelmeier et al. |
| 2003/0181801 | A1 | 9/2003 | Lasser et al. |
| 2003/0194050 | A1 | 10/2003 | Eberhard et al. |
| 2004/0122325 | A1 | 6/2004 | Chambers et al. |
| 2007/0223651 | A1 | 9/2007 | Wagenaar et al. |
| 2007/0276233 | A1 | 11/2007 | Besson et al. |
| 2008/0103387 | A1 | 5/2008 | Gross |
| 2008/0242979 | A1 | 10/2008 | Fisher et al. |
| 2012/0150034 | A1* | 6/2012 | DeFreitas ............ A61B 6/025 600/437 |
| 2013/0116570 | A1 | 5/2013 | Carson et al. |
| 2013/0237814 | A1 | 9/2013 | Marcovici |
| 2013/0281840 | A1 | 10/2013 | Vaughan et al. |
| 2014/0135623 | A1 | 5/2014 | Manak et al. |
| 2014/0180082 | A1 | 6/2014 | Evans et al. |
| 2015/0148670 | A1 | 5/2015 | Smith et al. |
| 2016/0166217 | A1 | 6/2016 | Davis et al. |
| 2016/0166234 | A1 | 6/2016 | Zhang et al. |

OTHER PUBLICATIONS

Partial European Search Report and Opinion issued in connection with corresponding EP Application No. 172094 77.3 dated May 24, 2018.

Extended European Search Report and Opinion issued in connection with corresponding EP Application No. 172094 77.3 dated Dec. 4, 2018.

Carson et al., "Dual Sided Automated Ultrasound System in the Mammographic Geometry", IEEE International Ultrasonics Symposium, pp. 2134-2137, Oct. 18-21, 2011.

Sinha et al., "Automated Ultrasound Scanning on a Dual-Modality Breast Imaging System: Coverage and Motion Issues and Solutions," Journal of Ultrasound in Medicine, vol. 26, No. 5, 2007, pp. 645-655.

Vaughan et al., "Testing a dual-modality system that combines full-field digital mammography and automated breast ultrasound", National Center for Biotechnology Information, pp. 498-505, Dec. 3, 2015.

Larson et al., "Automated Breast Ultrasound: Dual-Sided Compared with Single-Sided Imaging", National Center for Biotechnology Information, http://www.ncbi.nlm.nih.gov/pubmed/27264914, Jun. 2, 2016.

Kapur et al., "Fusion of Digital Mammography with Breast Ultrasound—a Phantom Study," Medical Imaging 2002, International Society for Optics and Photonics, pp. 526-537.

Padilla et al., "Breast Mass Characterization using 3D Automated Ultrasound as an Adjunct to Digital Breast Tomosynthesis: A Pilot Study," Journal of Ultrasound in Medicine, vol. 32, No. 1, Jan. 2013, pp. 93-104.

Li et al., "Effect of Gel Retainment Darn on Automated Ultrasound Coverage in a Dual-Modality Breast Imaging System," Journal of Ultrasound in Medicine, vol. 29, No. 7, Jul. 2010, pp. 1075-1081.

Carson, P. et al., "Local Compression in Automated Breast Ultrasound in the Mammographic Geometry," 2010 IEEE International Ultrasonics Symposium Proceedings, Oct. 11, 2010 (pp. 1787-1790).

* cited by examiner

SYSTEM AND METHOD FOR BREAST IMAGING

BACKGROUND

The field of the disclosure relates generally to breast imaging systems, and, more particularly, to breast imaging systems including ultrasound and x-ray using a dual-sided compression paddle system and the methods of operation for acquiring breast images.

Breast cancer screening is performed with x-ray imaging in either two-dimensional, i.e., mammography, and in recent years, tomosynthesis (three-dimensional x-ray). For many women, such x-ray screening is sufficient for generating images that are satisfactory for review by a medical professional. However, many women have a high percentage of dense breast tissues which do not show contrast versus cancerous tissues and additional screening is performed through ultrasound imaging. Ultrasound imaging is often performed in a supine position whereas the x-ray mammography is performed with the women upright with the breast in a compressed position. Such shifting of position of the patient shifts the shape and the tissue of the breast making any registration of the two imaging modalities difficult. As a result, significant discrepancies between the findings in the mammography and the ultrasound images may require further imaging to resolve and my lead to unnecessary biopsies. Therefore, it is highly desirable to perform the mammography or tomosynthesis imaging in the exact same positioning at the same time as the ultrasound imaging. To perform ultrasound imaging, the ultrasound probe must be in contact with the tissue or a coupling medium such as ultrasound gel or lotion or water. However, if the ultrasound gel is applied to the breast prior to taking the x-ray image it may result in artifacts in the x-ray image.

In addition, in order to achieve high x-ray image quality, either mammography or tomosynthesis, one must have as small of a distance between the x-ray detector and the breast as possible. Therefore, to preserve optimal image quality between x-ray imaging and ultrasound imaging one must move the ultrasound transducer and coupling medium between the x-ray source and/or detector and the breast.

Previous attempts to design breast screening systems that integrate both x-ray and ultrasound technologies have had not completely addressed the workflow and image quality needed in both the mammography and ultrasound. In previous examples, the woman's breast is compressed as for standard mammography imaging and the x-ray image acquired. Upon completion of the x-ray image the breast is scanned with the ultrasound probe on top of the compression paddle on the breast. This configuration gives very good mammography image quality. However, the ultrasound image quality is degraded as resolution is limited by the frequency of the ultrasound due to an inverse relationship between the frequency of the ultrasound signals and the penetration depth of the sound waves, i.e., the sound attenuation is proportional to the frequency and higher frequency ultrasound may not adequately penetrate the breast tissue. In most breast-compressed thicknesses the ultrasound frequency needed to fully penetrate the breast does not give sufficient imaging resolution to detect small masses and calcifications.

In other systems, where the breast is scanned from below, the ultrasound attenuation issue described above remains and additionally coupling medium for the ultrasound probe absorbs a significant portion of the x-rays after exposing the patient. This results in necessitating a higher x-ray dose to the patient. Furthermore the distance between the x-ray detector and the patient is increased. This may result in degradation of the x-ray image quality as well.

Dual sided scanning with ultrasound on a separate system in the mammography configuration has also been demonstrated. In this configuration the ultrasound image quality has been preserved. However, the workflow and image registration have proven difficult, since movement of the breast being imaged is likely. It is highly desirable to incorporate the high image quality of dual sided ultrasound scanning in the mammography configuration without requiring the use of a separate system. In order to perform dual sided ultrasound scanning of the breast on a mammography system, one solution is to include features that move the x-ray detector out of the way such that the ultrasound probe can be moved into position once x-ray imaging has been performed. However, for many known x-ray systems the detector is attached x-ray system gantry and does not move. For these systems an ultrasound only add-on is highly desirable.

BRIEF DESCRIPTION

In one aspect, an imaging assembly is provided. The imaging assembly includes a gantry and a compression system configured to receive and compress an object to be imaged. The compression system includes a first compression paddle coupled to the gantry and a second compression paddle coupled to the gantry. The imaging assembly also includes an x-ray detection device coupled to the gantry. The X-ray detection device is proximate the second compression paddle. The imaging assembly further includes an ultrasound system including a first ultrasound probe coupled to the first compression paddle. The first ultrasound probe is coupled to the first compression paddle. The first ultrasound probe is configured to acquire a first portion of the ultrasound image information of the object to be imaged. The ultrasound system also includes a second ultrasound probe coupled to the second compression paddle. The second ultrasound probe is configured to acquire a second portion of the ultrasound image information of the object to be imaged.

In a further aspect, a retrofit upgrade package for an installed legacy imaging system is provided. The retrofit upgrade package includes a compression system configured to receive and compress an object to be imaged. The compression system includes a first compression paddle configured to be coupled to a gantry and a second compression paddle configured to be coupled to the gantry. The retrofit upgrade package also includes an ultrasound system including a first ultrasound probe coupled to the first compression paddle. The first ultrasound probe is coupled to the first compression paddle. The first ultrasound probe is configured to acquire a first portion of ultrasound image information of the object to be imaged. The ultrasound system also includes a second ultrasound probe coupled to the second compression paddle. The second ultrasound probe is configured to acquire a second portion of the ultrasound image information of the object to be imaged.

In another aspect, a method of imaging an object is provided. The method includes positioning a first compression paddle to receive an object to be imaged and positioning a second compression paddle to extend over at least a portion of an x-ray detector. The method also includes positioning the object to be imaged between the first compression paddle and the second compression paddle. The method further includes generating x-ray image data of the object to be imaged. The method also includes translating the first compression paddle and the second compression paddle substantially synchronously with the object to be imaged remaining therebetween. The method further includes moving a first ultrasound probe across the first compression paddle and moving a second ultrasound probe across the second compression paddle substantially simultaneously.

DRAWINGS

These and other features, aspects, and advantages of the present disclosure will become better understood when the following detailed description is read with reference to the accompanying drawings in which like characters represent like parts throughout the drawings, wherein.

Figure 1:
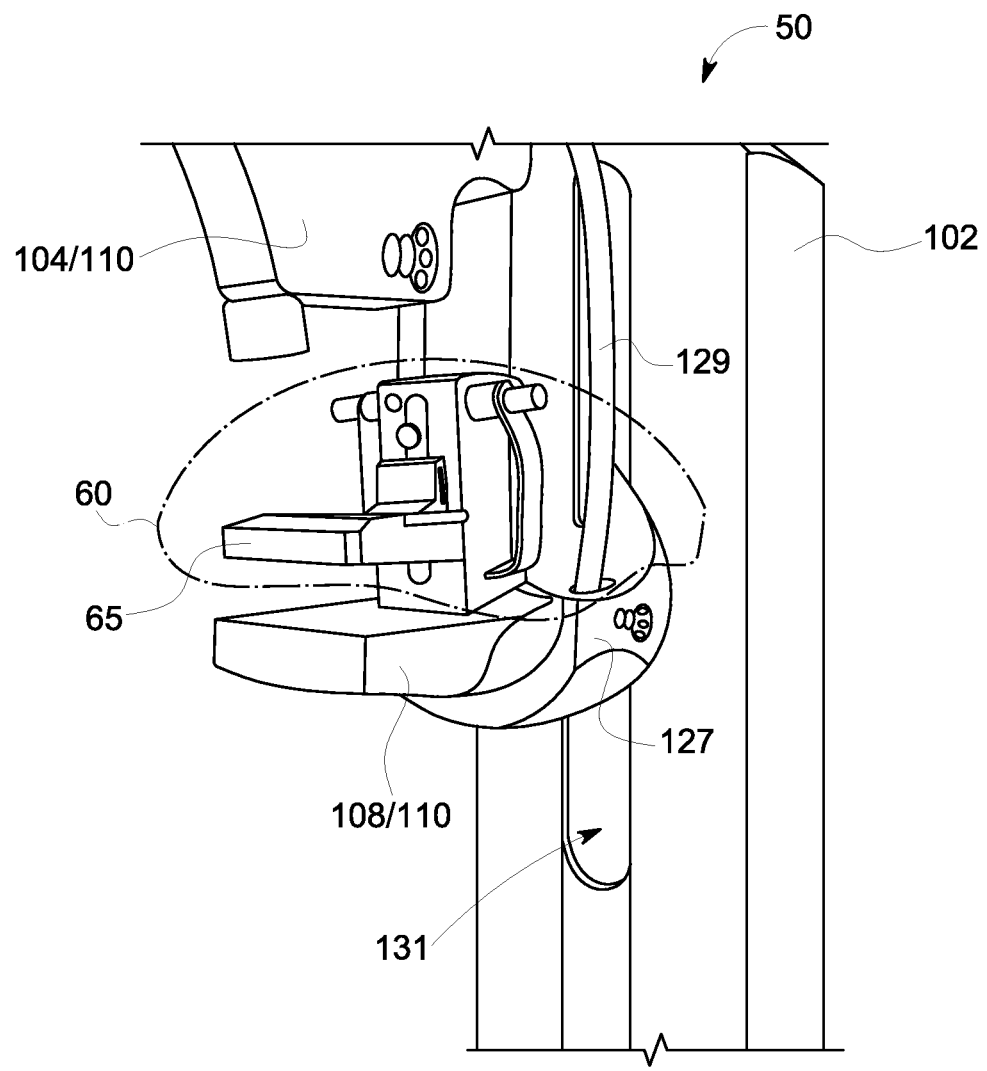
FIG. 1 is a perspective schematic view of a known breast imaging assembly.

Unless otherwise indicated, the drawings provided herein are meant to illustrate features of embodiments of the disclosure. These features are believed to be applicable in a wide variety of systems comprising one or more embodiments of the disclosure. As such, the drawings are not meant to include all conventional features known by those of ordinary skill in the art to be required for the practice of the embodiments disclosed herein.

DETAILED DESCRIPTION

In the following specification and the claims, reference will be made to a number of terms, which shall be defined to have the following meanings.

The singular forms "a", "an", and "the" include plural references unless the context clearly dictates otherwise.

"Optional" or "optionally" means that the subsequently described event or circumstance may or may not occur, and that the description includes instances where the event occurs and instances where it does not.

Approximating language, as used herein throughout the specification and claims, may be applied to modify any quantitative representation that could permissibly vary without resulting in a change in the basic function to which it is related. Accordingly, a value modified by a term or terms, such as "about", "approximately", and "substantially", are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

As used herein, the terms "processor" and "computer," and related terms, e.g., "processing device," "computing device," and "controller" are not limited to just those integrated circuits referred to in the art as a computer, but broadly refers to a microcontroller, a microcomputer, a programmable logic controller (PLC), and application specific integrated circuit, and other programmable circuits, and these terms are used interchangeably herein. In the embodiments described herein, memory may include, but it not limited to, a computer-readable medium, such as a random access memory (RAM), a computer-readable non-volatile medium, such as a flash memory. Alternatively, a floppy disk, a compact disc-read only memory (CD-ROM), a magneto-optical disk (MOD), and/or a digital versatile disc (DVD) may also be used. Also, in the embodiments described herein, additional input channels may be, but are not limited to, computer peripherals associated with an operator interface such as a mouse and a keyboard. Alternatively, other computer peripherals may also be used that may include, for example, but not be limited to, a scanner. Furthermore, in the exemplary embodiment, additional output channels may include, but not be limited to, an operator interface monitor.

Further, as used herein, the terms "software" and "firmware" are interchangeable, and include any computer program storage in memory for execution by personal computers, workstations, clients, and servers.

As used herein, the term "non-transitory computer-readable media" is intended to be representative of any tangible computer-based device implemented in any method of technology for short-term and long-term storage of information, such as, computer-readable instructions, data structures, program modules and sub-modules, or other data in any device. Therefore, the methods described herein may be encoded as executable instructions embodied in a tangible, non-transitory, computer-readable medium, including, without limitation, a storage device and/or a memory device. Such instructions, when executed by a processor, cause the processor to perform at least a portion of the methods described herein. Moreover, as used herein, the term "non-transitory computer-readable media" includes all tangible, computer-readable media, including, without limitation, non-transitory computer storage devices, including without limitation, volatile and non-volatile media, and removable and non-removable media such as firmware, physical and virtual storage, CD-ROMS, DVDs, and any other digital source such as a network or the Internet, as well as yet to be developed digital means, with the sole exception being transitory, propagating signal.

Furthermore, as used herein, the term "real-time" refers to at least one of the time of occurrence of the associated events, the time of measurement and collection of predetermined data, the time to process the data, and the time of a system response to the events and the environment. In the embodiments described herein, these activities and events occur substantially instantaneously.

In addition, as used herein, the terms "mammography", sometimes used to refer to a two-dimensional x-ray system, and "tomography", sometimes used to refer to a three-dimensional x-ray system, are used interchangeably. To facilitate clarity, the term "mammography" is used herein to generally refer to x-ray-based imaging systems, and, if necessary to differentiate the two systems, the term tomography, or a variant thereof, will be used.

The embodiments of the breast imaging systems described herein overcome many of the deficiencies of known x-ray and ultrasound imaging systems. The breast imaging systems described herein include enhancements to existing x-ray systems to include features that facilitate significant reductions in the shifting of the breast being imaged between the x-ray imaging and ultrasound imaging. Specifically, the breast imaging systems described herein integrate x-ray imaging and ultrasound imaging on the same machine with substantially the same compression induced on the breast being imaged and substantially similar positions for both images. As such, the breast imaging systems described herein are configured such that the detector is movable separate from the compression system such that the compression system and gantry may be moved in a synchronized fashion where the detector is lowered and the patient remains in compression and does not move significantly. Also, as such, the compression system couples to the mammography gantry as an attachment to the compression arm such that the compression system operates separately or in conjunction with the existing mammography compression system. More specifically, the embodiments described herein use two ultrasound probes and scan from the top of the breast and the bottom of the breast. Such dual-sided ultrasound scanning without interfering with the x-ray imaging detector is facilitated with a mechanism to move the breast upward with the upper and lower ultrasound transducers without hurting the woman while she is compressed.

In an alternative embodiment, the x-ray detector is moved downward more than 1 centimeter (cm) but less than 10 cm after the x-ray examination to facilitate providing room for the ultrasound transducer. Therefore, the breast can be as close as possible to the x-ray detector and by placing the x-ray detectors as close to the breast as possible, the quality of x-ray images is not degraded from a non-coupled examination. Once the x-ray portion of the exam is completed, the gantry, including the x-ray detector, is moved downward slightly and the two compression paddles move together such that the net effect on the breast is as small as possible. In addition, the two compression paddles are composed in part of a mesh material that contacts the breast to support it and apply compression and tissue immobilization. Further, small bladders are integrated into the compression paddles such that when the x-ray image is complete, the gantry moves, the paddles move and the little bladder in each paddle fills with ultrasound gel, water, or other ultrasound conductive material such that good contact with the breast for the ultrasound is facilitated. The systems described herein are compatible with existing mammography systems and may be installed as a retrofit upgrade without modification to the legacy x-ray system.

In the case of a retrofit upgrade to an existing x-ray mammography system, an add-on compression device may be used. This compression device will replace, or in some cases, work in conjunction with the existing compression system. The retrofit device attaches to the x-ray gantry as an attachment to the x-ray detector image receptor mechanism, preferably. The retrofit system consists of a compression device which includes one or two motors to drive two compression paddles independently. The compression paddles are such that the bottom compression paddle rests on the x-ray image receptor during x-ray imaging and is moved in conjunction with the top compression paddle before ultrasound imaging to allow room for the ultrasound transducer to move into contact with the breast. The compression paddles are controlled by a controller which also is in communication with the x-ray gantry or a patient lift device. The controller controls the movement of the compression paddles and gantry of the lift device such that the speed and distance movement of the compression paddles is parallel to that of the movement of the gantry or patient lift device. Once the x-ray portion of the exam is completed, the gantry including the x-ray detector are moved downward slightly and the two compression paddles move together such that the net effect on the breast is as small as possible and the compression plates remain parallel. Thus the patient breast location relative to the patient body does not move substantially.

Figure 2:
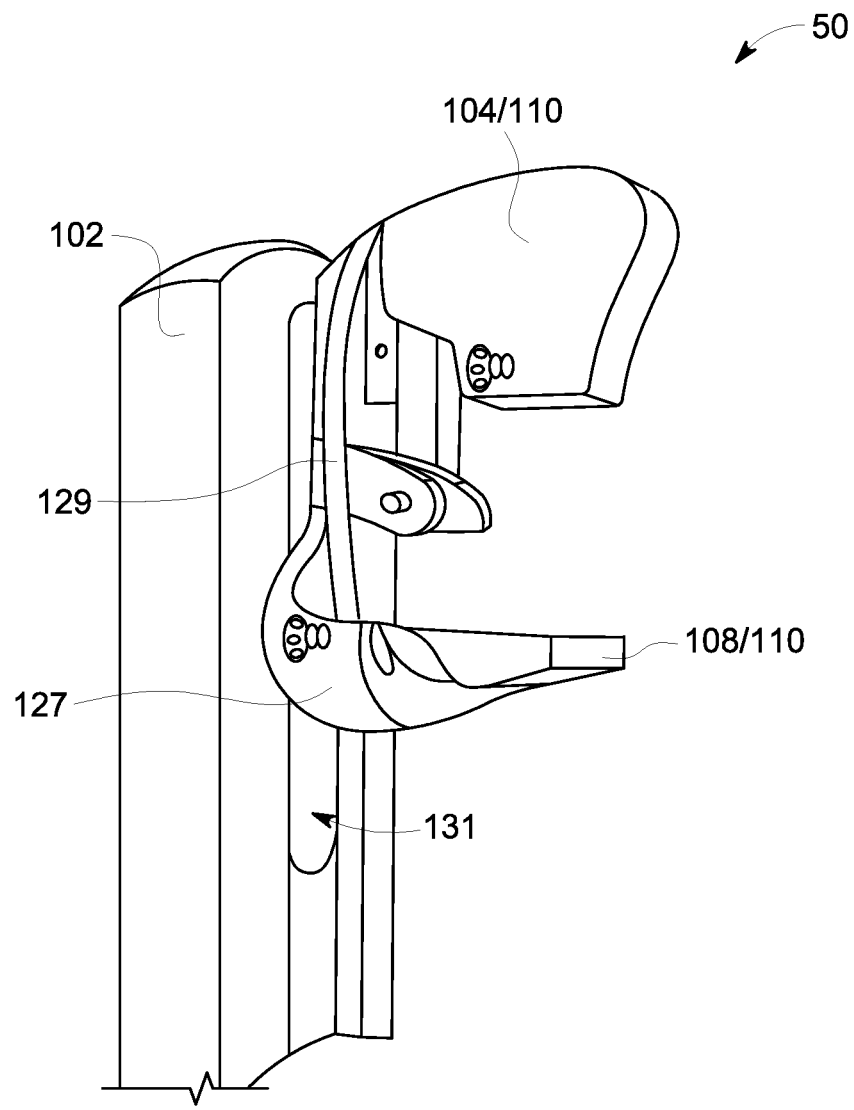
FIG. 2 is a another perspective schematic view of the known breast imaging assembly.

FIG. 1 is a perspective schematic view of a known breast imaging assembly 50. FIG. 2 is a another perspective schematic view of known breast imaging assembly 50. Known breast imaging system 50 includes a known combined compression system/ultrasound assembly 60 that includes a known combined compression paddle/ultrasound probe 65 (both only shown in FIG. 1). Breast imaging assembly 50 includes a gantry 102 and an x-ray source 104 coupled to gantry 102. Breast imaging assembly 50 further includes an x-ray detection device 108 that is aligned with x-ray source 104, where x-ray source 104, x-ray detection device 108, and gantry 102 define a mammography system 110. Breast imaging assembly 50 also includes a gantry translation cradle 127, a pair of cable conduits 129 coupling detector 108 to x-ray source 104, and a gantry translation slot 131 defined within gantry 102 that receives gantry translation cradle 127. Both combined compression/ultrasound assembly 60 and x-ray detection device 108 are coupled to gantry translation cradle 127, and assembly 60 and detector device 108 translate up and down with cradle 127 through slot 131 as necessary to adjust to a patient as a function of the patient's height and other anatomical features.

Figure 3:
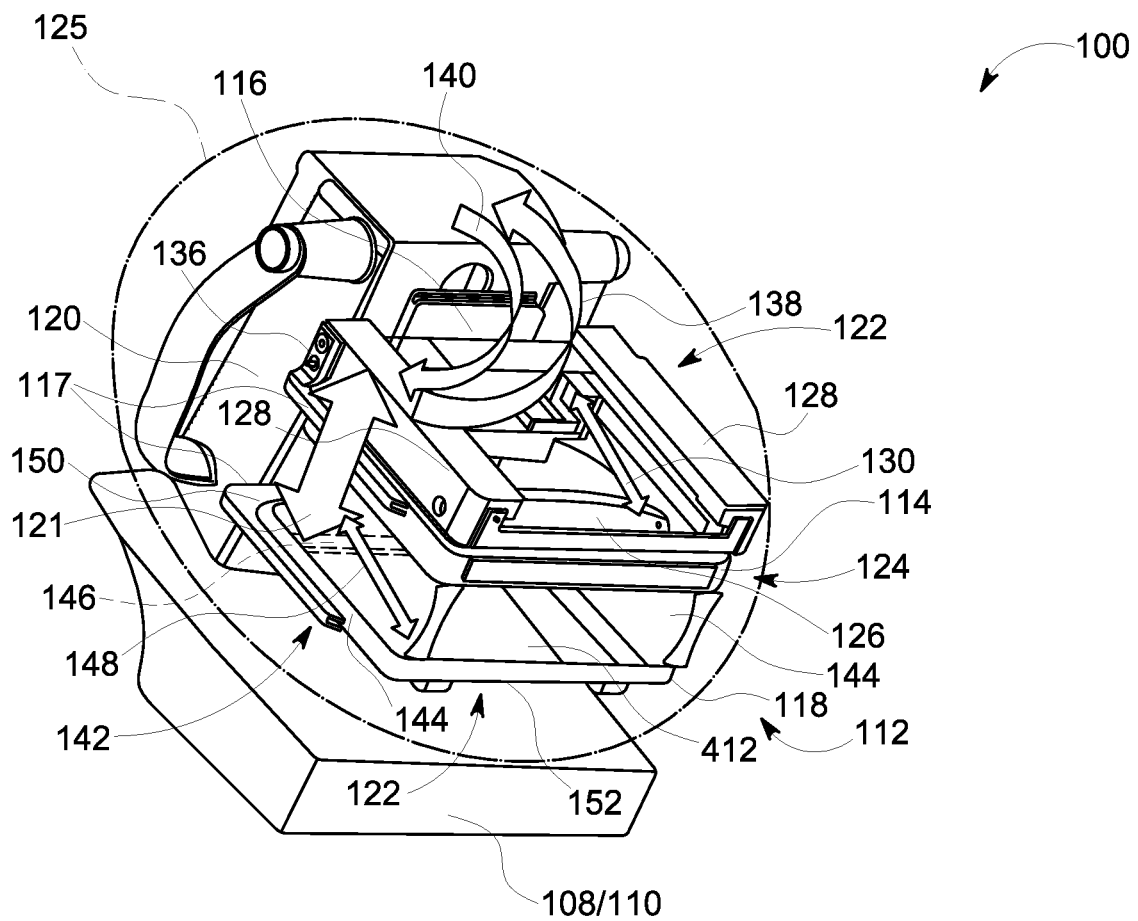
FIG. 3 is a front schematic perspective view of an exemplary breast imaging assembly.
Figure 4:
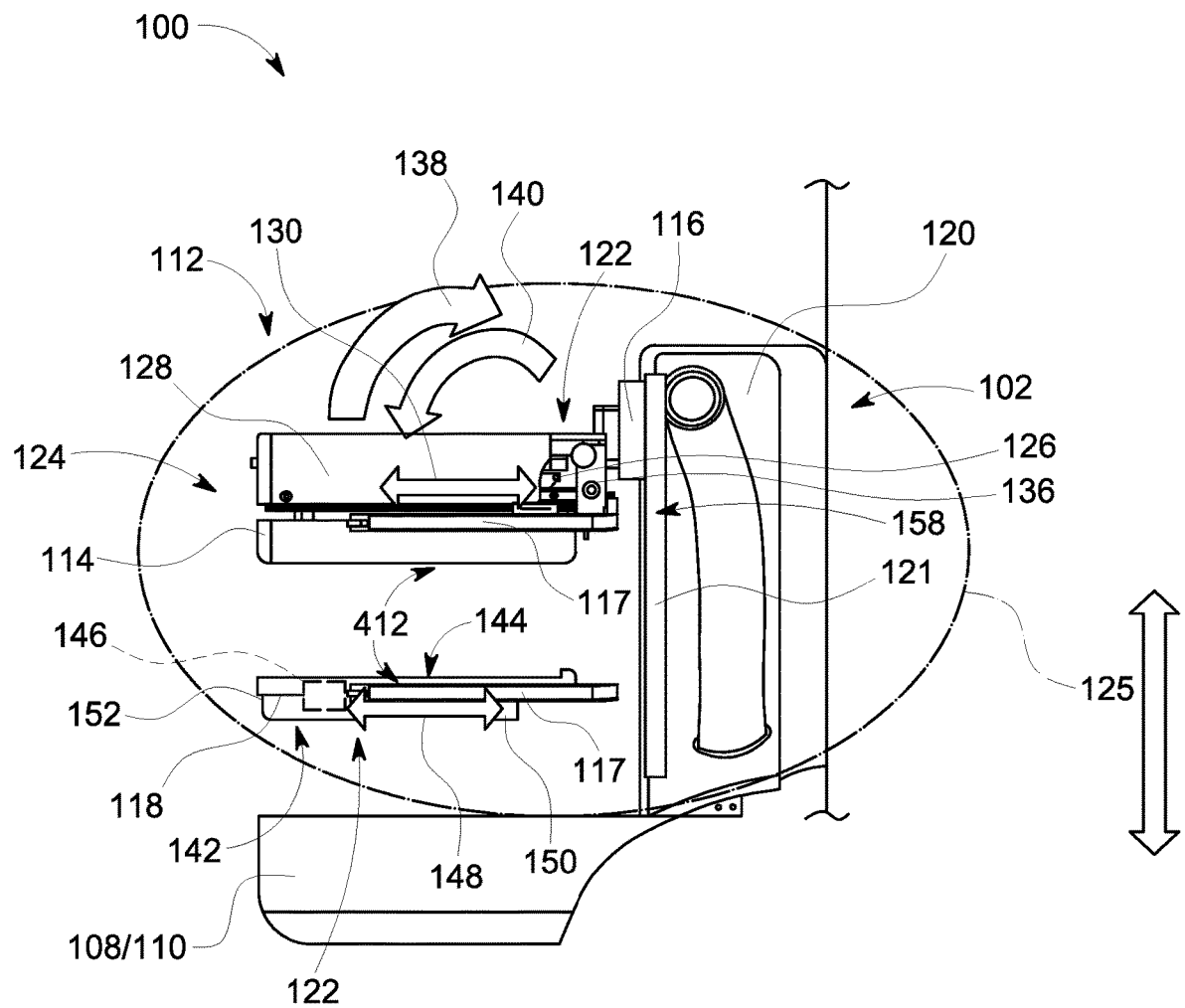
FIG. 4 is a side schematic view of the breast imaging assembly shown in FIG. 3.

FIG. 3 is a front schematic perspective view of an exemplary breast imaging assembly 100. FIG. 4 is a side schematic view of breast imaging assembly 100. Breast imaging assembly 100 includes gantry 102 and x-ray source 104 coupled to gantry 102, where is some embodiments, x-ray source 104 is substantially stationary, and in other embodiments, x-ray source 104 rotates upon an axis (not shown) to facilitate tomosynthesis imaging. Breast imaging assembly 100 further includes x-ray detection device 108 that is aligned with x-ray source 104, where x-ray source 104, x-ray detection device 108, and gantry 102 define mammography system 110.

In the exemplary embodiment, breast imaging assembly 100 includes a compression system 112 configured to receive and compress an object to be imaged, e.g., and without limitation, a woman's breast. Compression system 112 includes a first, i.e., upper compression paddle 114 translatably coupled to gantry 102 through a gantry mounting plate 116, and a translation back plate 120. Compression system 112 also includes a plurality of paddle positioning motors (not shown) positioned within gantry 102 and motor control features to facilitate precise positioning of paddles 114 and 118 (the motors and motor control are discussed further below). A paddle sliding engagement device 117 facilitates coupling paddle 114 to gantry mounting plate 116. Compression system 112 also includes a second, i.e., lower compression paddle 118 translatably coupled to gantry 102 though translation back plate 120. As described further below, translation back plate 120 facilitates vertical translation of lower compression paddle 118 and upper compression paddle 114 as indicated by bi-directional translation arrow 121.

Lower compression paddle 118 and x-ray detection device 108 are positioned proximate each other and lower compression paddle 118 rests on top of x-ray detection device 108 when breast imaging assembly 100 is in a mammography configuration (not shown in FIGS. 3 and 4) in contrast to an ultrasound configuration (as shown in FIGS. 3 and 4), where both configurations are discussed further below.

Also, in the exemplary embodiment, breast imaging assembly 100 includes an ultrasound probe sub-system 122. In the exemplary embodiment, compression system 112 and ultrasound probe-sub system 122 are integrated to define a combined compression/ultrasound assembly 125. Ultrasound probe sub-system 122 includes a first, i.e., upper ultrasound assembly 124 that includes a first, i.e., an upper probe track 128 to which upper ultrasound probe 126 is slidingly engaged, i.e., movably mounted on such that it can be moved across the top of paddle 114. Upper ultrasound probe 126 includes motion control features and devices (not shown) that facilitate moving probe 126 along upper probe track 128 in the directions indicated by bi-directional arrow 130. Upper ultrasound probe 126 is configured to acquire a first portion of the ultrasound image information of the object to be imaged.

Further, in the exemplary embodiment, breast imaging assembly 100 includes gantry translation cradle 127 (shown in FIGS. 1 and 2), cable conduits 129 (shown in FIGS. 1 and 2) coupling detector 108 to x-ray source 104, and gantry translation slot 131 (shown in FIGS. 1 and 2) defined within gantry 102 that receives gantry translation cradle 127. Both combined compression/ultrasound assembly 125 and x-ray detection device 108 are coupled to gantry translation cradle 127, and assembly 125 and detector device 108 translate up and down with cradle 127 through slot 131 as necessary to adjust to a patient as a function of the patient's height and other anatomical features. Therefore, combined compression/ultrasound assembly 125 is configured to replace combined compression system/ultrasound assembly 60 (shown in FIG. 1) within gantry translation cradle 127 and combined compression/ultrasound assembly 125 is compatible with known x-ray detection device 108, also configured to reside in gantry translation cradle 127. As such, combined compression/ultrasound assembly 125 is configured to facilitate retrofit upgrades to known breast imaging assembly 50 (shown in FIG. 1) and other known breast imaging assemblies and combined compression/ultrasound assembly 125 may be installed on legacy breast imaging assemblies as at least a portion of a retrofit upgrade package.

Figure 5:
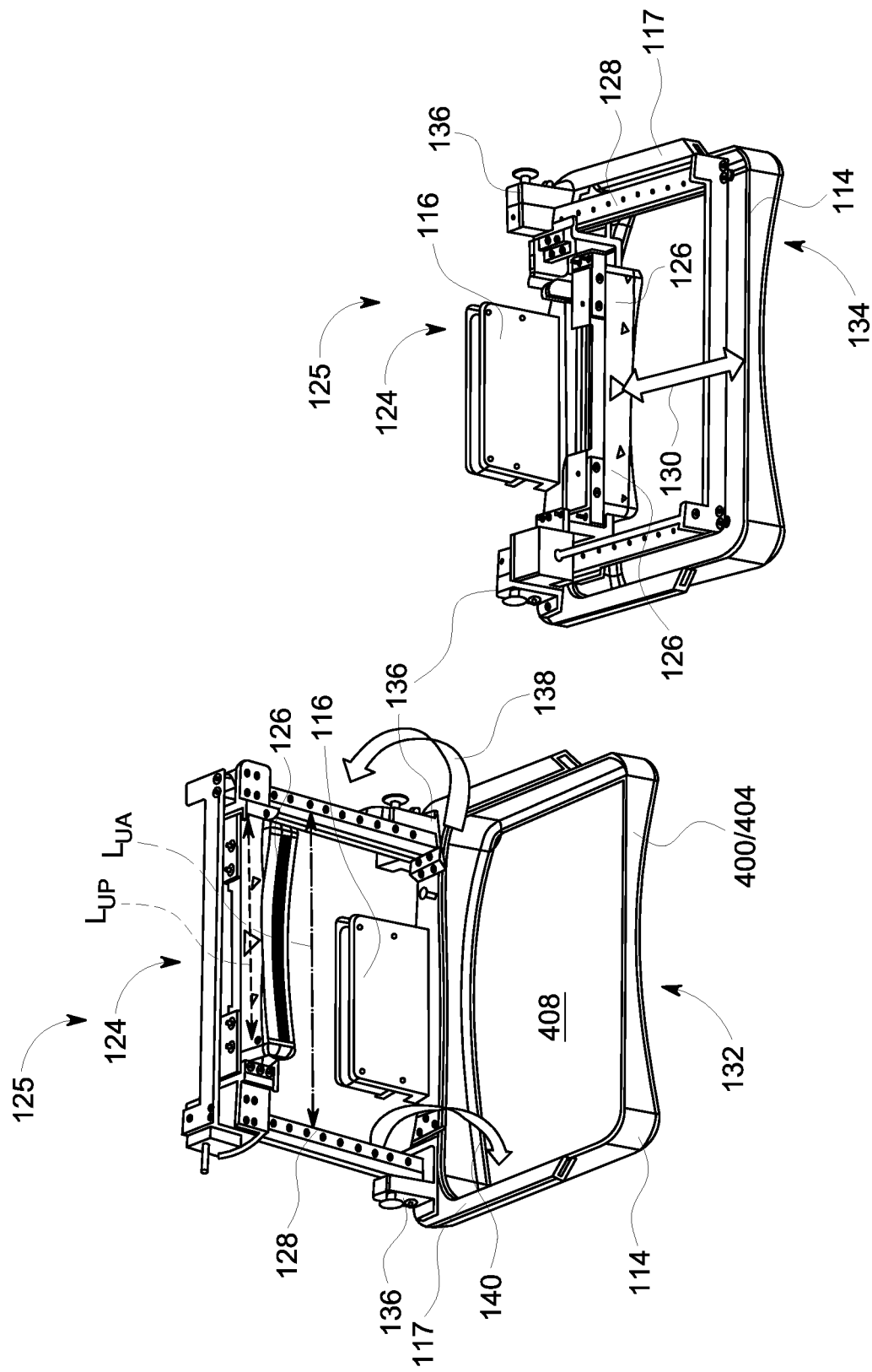
FIG. 5 is a schematic perspective view of an exemplary upper ultrasound probe assembly that may be used with the breast imaging assembly shown in FIGS. 3 and 4.

FIG. 5 is a schematic perspective view of upper ultrasound assembly 124 in a mammography configuration 132 (not shown in FIGS. 3 and 4) and an ultrasound configuration 134 (also, as shown in FIGS. 3 and 4). Upper ultrasound assembly 124 includes a pivot mechanism 136 that pivotably mounts upper ultrasound assembly 124 to upper compression paddle 114. Upper ultrasound assembly 124 is configured to be positioned between x-ray source 104 and x-ray detector 108 (both shown in FIGS. 3 and 4), where upper ultrasound assembly 124 is configured to pivot, i.e., flip from a first position, i.e., ultrasound configuration 134 extending over at least a portion of upper compression paddle 114 to a second position, i.e., mammography configuration 132 proximate gantry 102. Arrow 138 indicates this pivoting movement. In mammography configuration 132, upper ultrasound probe 126 is substantially removed from an x-ray beam (not shown) emanated from x-ray source 104 toward x-ray detection device 108 such that upper ultrasound probe 126 does not interfere with tomographic imaging of the object being imaged. Upper ultrasound assembly 124 is also configured to pivot from mammography configuration 132 to ultrasound configuration 134 to facilitate acquisition of the first portion of the ultrasound image information of the object to be imaged. Arrow 140 indicates this pivoting movement.

Upper ultrasound assembly 124 has a lateral length $L_{UA}$ and upper ultrasound probe 126 has a lateral length $L_{UP}$. Lateral length $L_{UA}$ and lateral length $L_{UP}$ have any values that enable operation of breast imaging assembly 100 as described herein. For example, and without limitation, lateral length $L_{UA}$ is approximately 30 centimeters (cm) from the left track 128 to the right track 128 and lateral length $L_{UP}$ is approximately 15 cm. Typically, when one sweep of probe 126 is necessary, upper ultrasound probe 126 moves in a centered configuration along tracks 128 through upper ultrasound probe 126. However, if lateral length $L_{UP}$ is not long enough to cover an entire breast (not shown in FIG. 5) laterally, then a second sweep may be performed. This can be configured by a technologist before the scan begins. If two sweeps of probe 126 are to be performed, probe 126 will be shifted to one side of assembly 124, a first scan performed, and then probe 126 will shift to the opposite side of assembly 124 and a second scan will be performed. The associated ultrasound imaging software is configured to facilitate seamless integration of the two sweeps of probe 126 without the need to reposition the patient. Alternatively, lateral length $L_{UP}$ is approximately 30 cm to facilitate more rapid scanning and seamless integration of the two sweeps of the probe. This concept can be used in single side or even supine imaging system. In some alternative embodiments, sweeps of probe 126 are lateral, i.e., from side to side. Such embodiments will require reconfiguration of upper ultrasound assembly 124, e.g., tracks 128 and ultrasound probe 126 rotated 90 degrees to facilitate lateral, i.e., left-to-right scans rather than those front-to-back scans performed by the exemplary embodiment. For many breasts, if the sweep is performed side to side, only one sweep will be needed for reason including, and without limitation, substantially asymmetric compression, breast size, and breast tissue density.

Referring again to FIGS. 3 and 4, ultrasound probe sub-system 122 includes a second, i.e., lower ultrasound assembly 142 that includes a second, i.e., a lower probe track 144 to which a lower ultrasound probe 146 is slidingly engaged, i.e., movably mounted on. In some embodiments, lower ultrasound assembly 142 is removably coupled to lower compression paddle 118 such that lower ultrasound assembly 142 is easily and quickly installed and removed from lower compression paddle 118 for those embodiments that may require some assembly and disassembly between x-ray and ultrasound imaging. Lower ultrasound probe 146 includes motion control features and devices (not shown) that facilitate moving probe 146 along lower probe track 144 in the directions indicated by bi-directional arrow 148. In the exemplary embodiment, lower ultrasound assembly 142 and lower ultrasound probe 146 are different in construction and configuration as compared to upper ultrasound assembly 124 and upper ultrasound probe 126. For example, and without limitation, upper ultrasound assembly 124 may be curved and lower ultrasound assembly 142 straight (as described further with respect to FIG. 11), and upper ultrasound probe 126 may be taller due to additional electronics while lower ultrasound probe 146 may be thinner and wider. Alternatively, lower ultrasound assembly 142 and lower ultrasound probe 146 are similar in construction and configuration as upper ultrasound assembly 124 and upper ultrasound probe 126, respectively.

Lower ultrasound probe 146 is configured to acquire a second portion of the ultrasound image information of the object to be imaged. Upper ultrasound probe 126 and lower ultrasound probe 146 are configured to move substantially synchronously to acquire the first portion and the second portion of the ultrasound image information of the object to be imaged substantially simultaneously. Alternatively, any sequence of operation of ultrasound probes 126 and 146 that enables operation of breast imaging assembly 100 as described herein is used, including, without limitation, series sequential operation, i.e., either of probes 126 and 146 first, followed by the other, and operation for through transmission, i.e., acoustic enhancement. In addition, to facilitate obtaining tomography images, lower compression paddle 118 includes a first side 150 proximate gantry 102 and a second side 152 opposite first side 150 in the direction of arrow 148, where ultrasound probe 146 is parked proximate first side 150 when x-ray source 104 emanates the x-ray beam toward x-ray detection device 108 while breast imaging assembly 100 is in mammography configuration 132.

Figure 6:
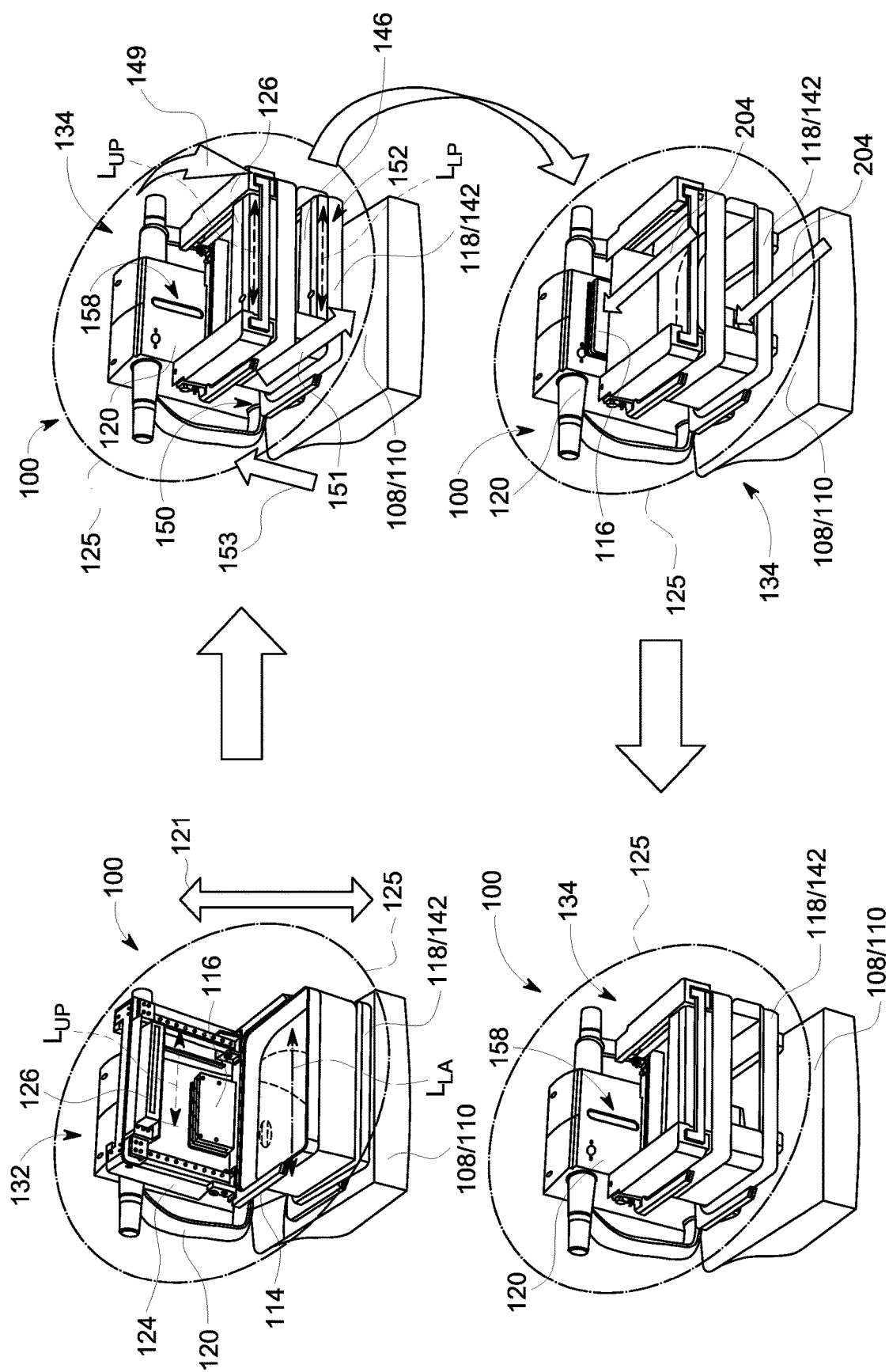
FIG. 6 is a schematic perspective view of the breast imaging assembly shown in FIGS. 3 and 4 in a plurality of configurations.

FIG. 6 is a schematic perspective view of the breast imaging assembly 100 shown in a plurality of configurations, i.e., mammography configuration 132 and ultrasound configuration 134. Specifically, in operation, breast imaging assembly 100 is initially shown in mammography configuration 132 with upper ultrasound assembly 124 in the raised position, lower ultrasound probe 146 (shown in FIGS. 3 and 4) in the parked position adjacent gantry 102 (shown in FIGS. 1 and 2) on first side 150 of lower compression paddle 118, and lower compression paddle 118 with lower ultrasound assembly 142 resting on x-ray detection device 108, a woman's breast (not shown in FIG. 6) is positioned between compression paddles 114 and 118.

Lower ultrasound probe assembly 142 has a lateral length $L_{LA}$ and lower ultrasound probe 146 has a lateral length $L_{LP}$. Lateral length $L_{LA}$ and lateral length $L_{LP}$ have any values that enable operation of breast imaging assembly 100 as described herein. For example, and without limitation, lateral length $L_{LA}$ is approximately 30 cm from the left track 144 to the right track 144 and lateral length $L_{LP}$ is approximately 15 cm. Notably, lateral length $L_{LA}$ will have a value such that the surface area of lower ultrasound probe assembly 142 is greater than the active area of x-ray detection device 108. Typically, when one sweep of probe 146 is necessary, lower ultrasound probe 146 moves in a centered configuration along tracks 144 through upper ultrasound probe 124. However, if lateral length $L_{LP}$ is not long enough to cover an entire breast (not shown in FIG. 4) laterally, then a second sweep may be performed. This can be configured by a technologist before the scan begins. If two sweeps of probe 146 are to be performed, probe 146 will be shifted to one side of assembly 142, a first scan performed, and then probe 146 will shift to the opposite side of assembly 142 and a second scan will be performed. The associated ultrasound imaging software is configured to facilitate seamless integration of the two sweeps of probe 146 without the need to reposition the patient. Alternatively, lateral length $L_{LP}$ is approximately 30 cm to facilitate more rapid scanning and seamless integration of the two sweeps of the probe. This concept can be used in single side or even supine imaging system. In some alternative embodiments, sweeps of probe 126 are lateral, i.e., from side to side. For many breasts, if the sweep is performed side to side, only one sweep will be needed.

In some alternative embodiments (described further below), upper probe track 128 (shown in FIGS. 3-5) (to which upper ultrasound probe 126 is slidingly engaged) is rounded upward proximate a human patient (not shown in FIG. 6). Similarly, in some alternative embodiments, lower probe track 144 (shown in FIGS. 3-5) (to which lower ultrasound probe 146 is slidingly engaged) is rounded downward proximate the human patient.

As breast imaging assembly 100 shifts from mammography configuration 132 to ultrasound configuration 134, upper ultrasound assembly 124 pivots down to the lowered position as indicated by arrow 149. Also, as breast imaging assembly 100 shifts from mammography configuration 132 to ultrasound configuration 134, lower ultrasound probe 146 moves from the parked position on first side 150 of lower compression paddle 118 toward second side 152 of lower compression paddle 118 as indicated by arrow 151. In some alternative embodiments, lower ultrasound probe 146 may be "parked" proximate second side 152 of lower compression paddle 118. Further, as breast imaging assembly 100 shifts from mammography configuration 132 to ultrasound configuration 134, lower compression paddle 118 with lower ultrasound assembly 142 translates, i.e., raises upward from x-ray detection device 108 toward x-ray source 104 (shown in FIGS. 1 and 2) substantially synchronously with upper compression paddle 114 as shown by arrow 153. As described above, in some alternative embodiments, any sequence of operation of ultrasound probes 126 and 146 that enables operation of breast imaging assembly 100 as described herein is used, including, without limitation, series sequential operation, i.e., either of probes 126 and 146 first, followed by the other. The range of translating motion is within, and including, approximately 1 cm and 3 cm, with the exemplary embodiment translating approximately 2 cm. Further, in the exemplary embodiment, with a woman's breast compressed between compression paddles 114 and 118, the pivoting of upper ultrasound assembly 124, movement of lower ultrasound probe 146, and translation of paddles 114 and 118 occur substantially simultaneously and synchronously to facilitate decreasing the amount of time a woman must maintain her breasts between compression paddles 114 and 118 to reduce discomfort. Alternatively, such pivoting, moving, and translating are executed in any sequence that enables operation of breast imaging assembly 100 as described herein.

Figure 7:
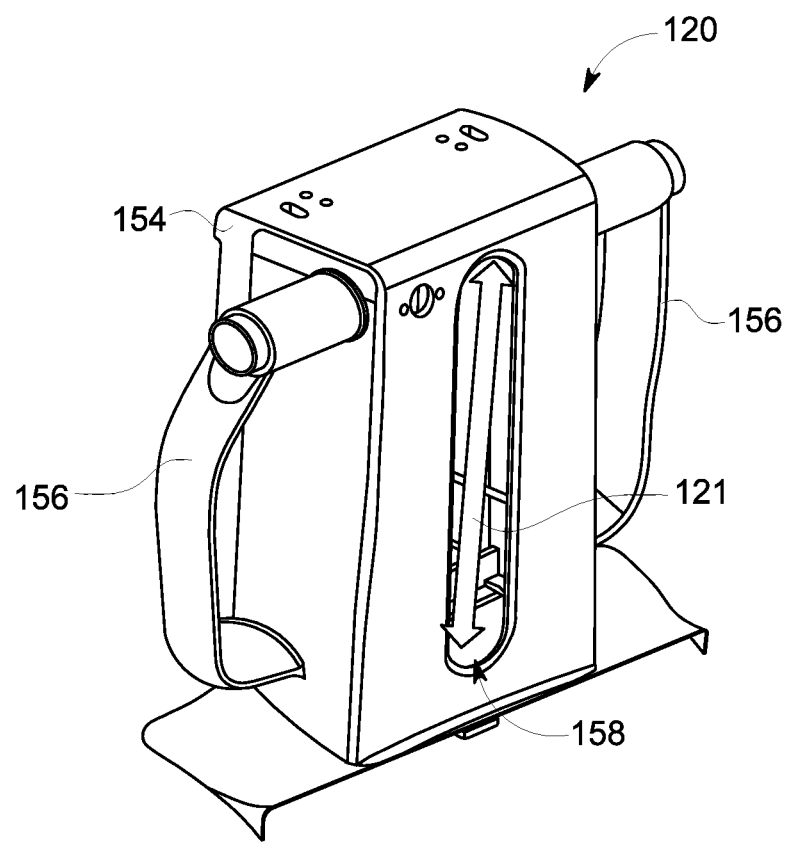
FIG. 7 is a schematic perspective view of an exemplary translation back plate that may be used with the breast imaging assembly shown in FIGS. 3 and 4.

FIG. 7 is a schematic perspective view of translation back plate 120 used with breast imaging assembly 100 (shown in FIGS. 3, 4, and 6). Translation back plate 120 includes a casing 154, a pair of lateral handles 156, and a translation slot 158 defined in casing 154. Translation slot 158 receives upper compression paddle 114 (with upper ultrasound assembly 124 coupled thereto) and lower compression paddle 118 (with lower ultrasound assembly 142 coupled thereto) therein (all shown in FIGS. 3, 4, and 5). Casing 154 receives and houses equipment (not shown) necessary for the operation of breast imaging assembly 100 including compression system 112, mammography system 110, and ultrasound probe sub-system 122 (all shown in FIGS. 3 and 4) as described herein. Such equipment includes, without limitation, one or more translation drive motors (electric, hydraulic, or pneumatic) for synchronously translating upper compression paddle 114 and lower compression paddle 118 up and down as indicated by bi-directional translation arrow 121. There may be one or two motors for compression system 112, e.g., one motor for upper compression paddle 114 and one motor for lower compression paddle 118, where the motors may be configured to operate either independently or synchronously.

Such equipment also includes, without limitation, one or more translation drive motors (electric, hydraulic, or pneumatic) to pivot upper ultrasound assembly 124 between the lowered position and the raised position. Such equipment further includes, without limitation, movement drive motors (electric, hydraulic, or pneumatic) to move lower ultrasound probe 146 between first side 150 of lower compression paddle 118 and second side 152 of lower compression paddle 118. Moreover, in some embodiments, such equipment includes, without limitation, power supplies and/or converters and controller(s) to regulate and control the operation of breast imaging assembly 100 as described herein.

Figure 8:
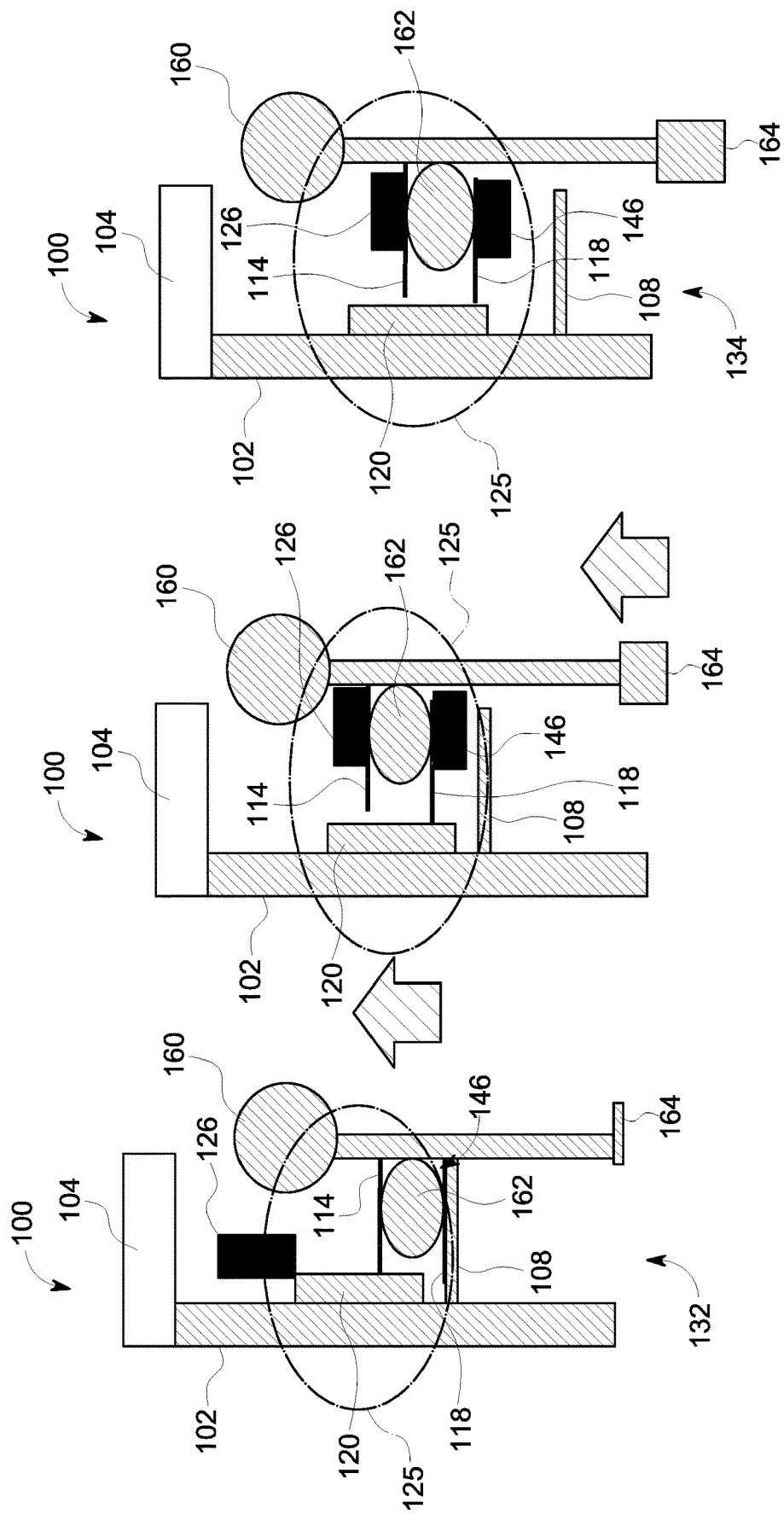
FIG. 8 is a schematic view of an exemplary patient using the breast imaging assembly shown in FIGS. 3 and 4 with an exemplary lift and support device.

FIG. 8 is a schematic view of an exemplary human patient 160 using breast imaging assembly 100. A breast 162 of patient 160 is positioned between upper compression paddle 114 and lower compression paddle 118. Also, in some embodiments, patient 160 is positioned on a translatable device 164, i.e., a lift and support device 164. In some embodiments, translatable device 164 is a translatable platform and patient 160 stands on device 164. Device 164 is configured to translate synchronously with compression paddles 114 and 118 as breast imaging assembly 100 shifts from mammography configuration 132 to ultrasound configuration 134 as described above. Therefore, breast imaging assembly 100 facilitates execution of both x-ray scans and ultrasound scans while breast 162 remains substantially compressed with a similar compression during both procedures. In general, some compression relaxation may be performed during the shift from the x-ray scan configuration to the ultrasound scan configuration to facilitate the compression paddle motion, to improve ultrasound probe contact with the breast or to improve patient comfort for example. During the x-ray examination the compression will be such to shape the breast and reduce the x-ray radiation dose in 3D imaging and for 2D imaging to reduce the overlapping tissue. The compression during the ultrasound examination will maintain the lateral position of the breast to improve image registration.

Operation of upper compression paddle 114, lower compression paddle 118, and lift and support device 164 is synchronized through an integrated controller or control system (neither shown in FIG. 8). Alternatively, gantry 102 is configured to translate in one direction while paddles 114 and 118 translate in the opposite direction through the associated control scheme such that the position of breast 162 is substantially constant, given the general considerations described above.

Figure 9:
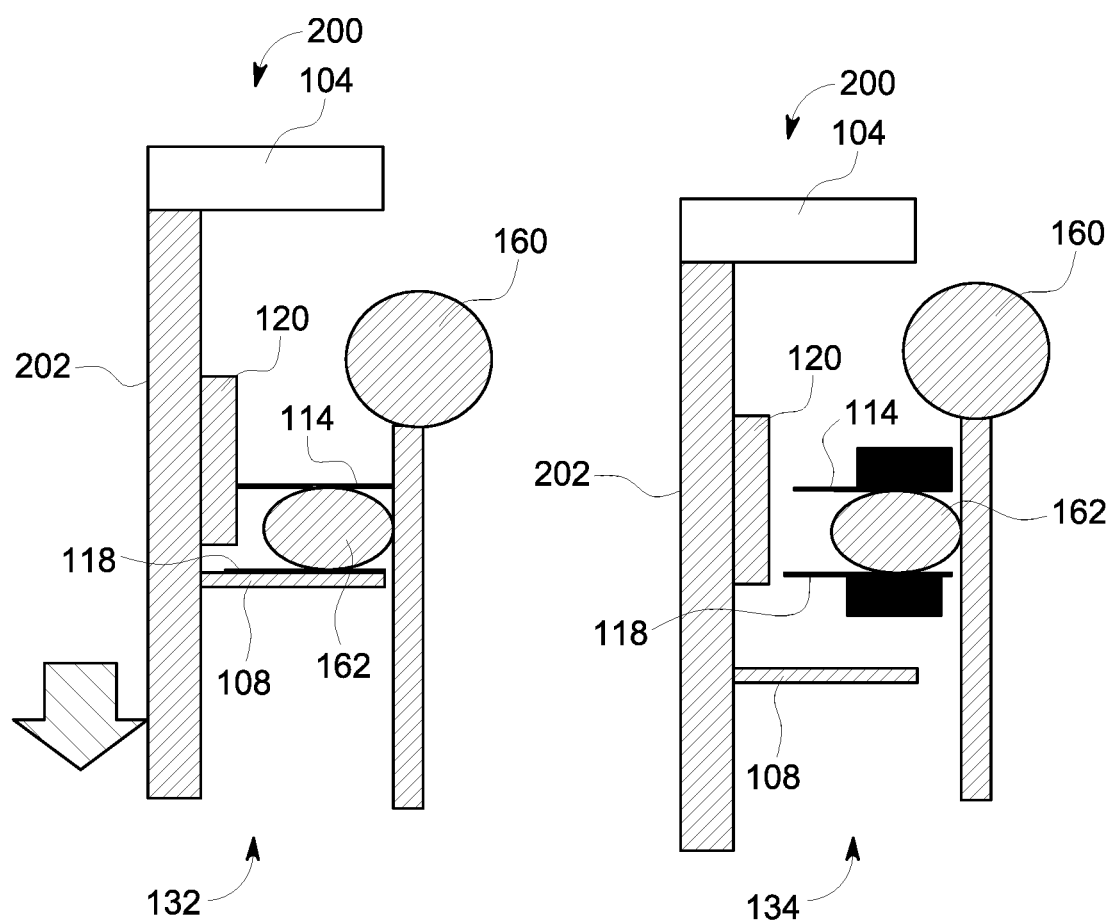
FIG. 9 is a schematic view of the patient shown in FIG. 8 using an alternative breast imaging assembly with gantry control synchronized to the compression system.

FIG. 9 is a schematic view of patient 160 using an alternative breast imaging assembly 200 that includes an alternative gantry 202. In contrast to breast imaging assembly 100 and gantry 102, breast imaging assembly 200 and gantry 202 include additional control features, such as additional hardware, software, and firmware, to translate gantry 202 upward and downward while translating upper compression paddle 114 and lower compression paddle 118 in the opposite directions such that paddles 114 and 118 are substantially stationary with respect to patient 160 and breast 162. In operation of breast imaging assembly 200, rather than solely translating upper compression paddle 114 and lower compression paddle 118 up and down to translate lower compression paddle 118 away from x-ray detection device 108, gantry 202, with x-ray detection device 108 coupled thereto, translates downward such that x-ray detection device 108 is lowered away from lower compression paddle 118. The range of translating motion in this alternative embodiment is within, and including, approximately 1 centimeter (cm) and 3 cm, with this alternative embodiment translating approximately 2 cm. Further, in this alternative embodiment, upper compression paddle 114 and lower compression paddle 118 are effectively stationary with any small relative movement of paddles 114 and 118 with respect to breast 162 provided to facilitate the comfort of the patient.

Referring again to FIG. 6, in operation of breast imaging assembly 100, once breast imaging assembly 100 is in ultrasound configuration 134, upper ultrasound assembly 124 and lower ultrasound assembly 142 move from proximate patient 160 (shown in FIGS. 8 and 9) toward gantry 102 substantially simultaneously as shown by arrows 204 while scanning breast 162 (shown in FIGS. 8 and 9) using ultrasound techniques, including, without limitation, reflection mode and transmission mode. Transmission mode may be facilitated by the use of a lower frequency ultrasound probe than for reflection mode. Once ultrasound scanning is complete, upper ultrasound assembly 124 returns to position proximate patient 160 and lower ultrasound assembly 142 remains in the parked position proximate gantry 102 (as described above). Also, upper compression paddle 114 and lower compression paddle 118 are separated to release breast 162 from compression and breast imaging assembly 100 is restored to mammography configuration 132 for either the other breast or the next patient. The compression on breast 162 will automatically be released when the ultrasound scanning is complete. The data from the ultrasound will be sent for reconstruction and the images reconstructed together to form a 3D ultrasound image of the breast.

Figure 10:
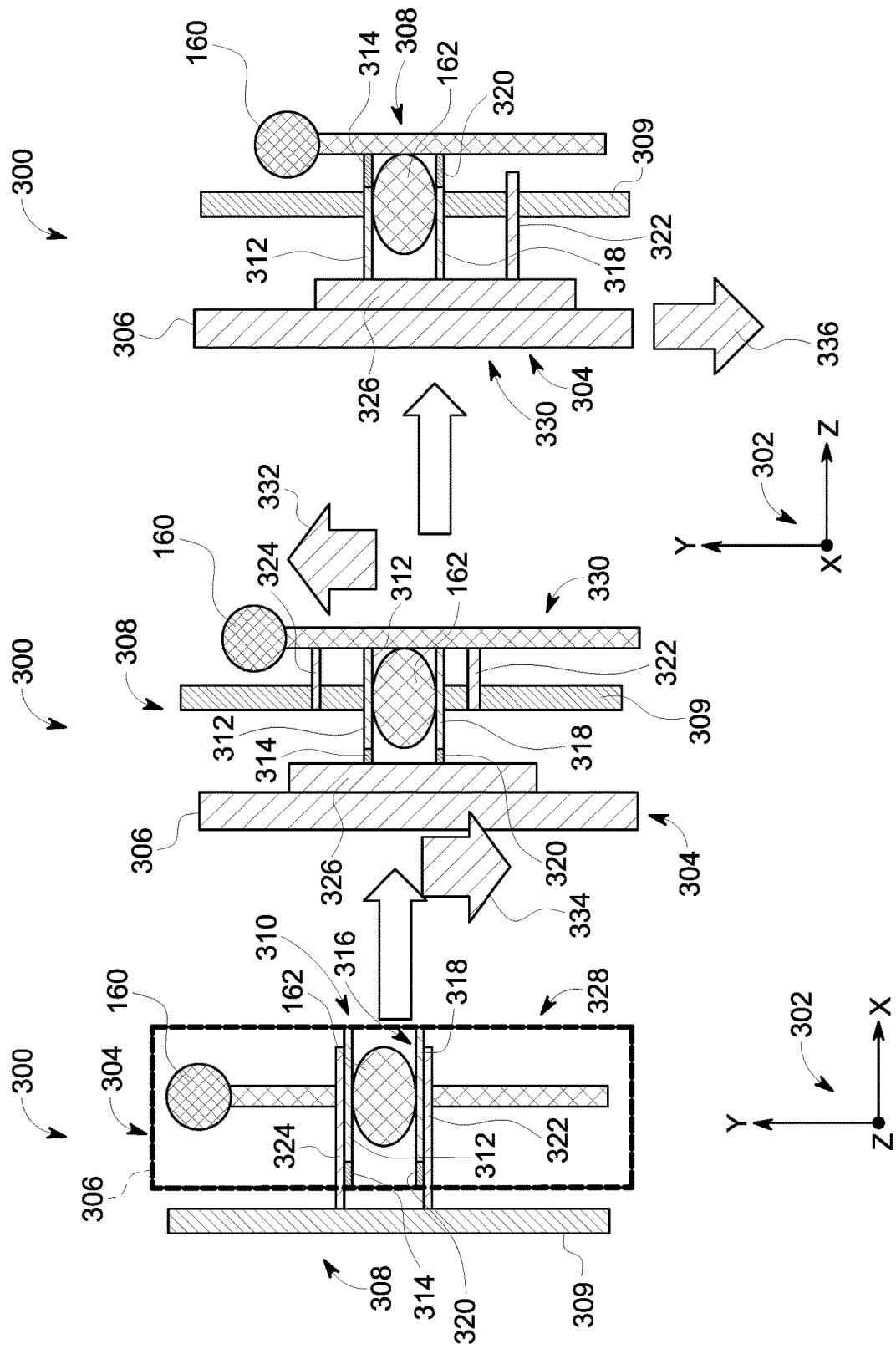
FIG. 10 is a schematic view of the patient shown in FIGS. 8 and 9 using another alternative breast imaging assembly.

FIG. 10 is a schematic view of patient 160 using another alternative breast imaging assembly 300. A coordinate system 302 with an X-axis, a Y-axis, and a Z-axis is used. Breast imaging assembly 300 includes an ultrasound stand system 304. Ultrasound stand system 304 includes a compression stand gantry 306 that is shown in phantom in the left illustration to clarify that human patient 160 is behind gantry 306 and facing toward the reader of this disclosure in the direction of the z-axis. In contrast to previous breast imaging assemblies 100 (shown in FIGS. 3, 4, 6 and 8) and 200 (shown in FIG. 9), gantry 306 is primarily configured for ultrasound stand system 304 that is substantially separated from an independent mammography system 308. Mammography system 308 includes a mammography gantry 309 and is shown to the right of human patient 160 in the direction of the x-axis. As such, ultrasound stand system 304 and mammography system 308 are shown substantially orthogonal to each other. In some embodiments, mammography system 308 is fixedly mounted proximate ultrasound stand system 304. In other embodiments, mammography system 308 is portable, e.g., mounted on wheels to facilitate convenient removal from breast imaging assembly 300 when x-ray imaging is not desired.

In this alternative embodiment, ultrasound stand system 304 also includes an upper (first) ultrasound assembly 310 that includes an upper (first) ultrasound paddle 312 and an upper (first) ultrasound probe 314. Ultrasound stand system 304 further includes a lower (second) ultrasound assembly 316 that includes a lower (second) ultrasound paddle 318 and a lower (second) ultrasound probe 320.

Also, in this alternative embodiment, mammography system 308 also includes an x-ray detection device 322 and an x-ray source (not shown). Mammography system 308 further includes an x-ray upper paddle 324. X-ray detection device 322 and x-ray upper paddle 324 are translatably coupled to mammography gantry 309 through a translation back plate (not shown) similar to translation back plate 120 (shown in FIGS. 3 and 4). Similarly, upper ultrasound assembly 310 and lower ultrasound assembly 316 are translatably coupled to compression stand gantry 309 though a translation back plate 326 that is also similar to translation back plate 120.

In operation of this alternative embodiment, breast imaging assembly 300 starts in a mammography configuration 328. In mammography configuration 328, human patient 160 has breast 162 compressed through upper ultrasound paddle 312 and lower ultrasound paddle 318. Also, in mammography configuration 328, x-ray upper paddle 324 rests directly on top of upper ultrasound paddle 312 and lower ultrasound paddle 318 rests on top of x-ray detection device 322. Once the x-ray portion of the breast exam is completed, breast imaging assembly 300 shifts from mammography configuration 328 to an ultrasound configuration 330. To start the shift, one or more translation drive motors (electric, hydraulic, or pneumatic) (not shown) translates x-ray upper paddle 324 through translation back plate 326 upward and away from upper ultrasound paddle 312 as shown by arrow 332. Similarly, one or more translation drive motors (electric, hydraulic, or pneumatic) (not shown) translates mammography gantry 309 and x-ray detection device 322 through the associated translation back plate downward and away from lower ultrasound paddle 318 as shown by arrow 334. Breast 162 remains compressed through upper ultrasound paddle 312 and lower ultrasound paddle 318. Further, to complete the shift in configuration, X-ray upper paddle 324 is retracted away from patient 160, or removed from the associated translation back plate and mammography gantry 309, and compression stand gantry 306 shifts downward approximately 2 cm as indicated by arrow 336 while paddles 312 and 318 are maintained substantially stationary with respect to breast 162.

In addition, with X-ray upper paddle 324 out of the way, upper ultrasound assembly 310 with upper ultrasound paddle 312 and upper ultrasound probe 314 are moved automatically or manually by the technologist on compression stand gantry 309. Similarly, with x-ray detection device 322 out of the way, lower ultrasound assembly 316 with lower ultrasound paddle 318 and lower ultrasound probe 320 are moved automatically or manually by the technologist on compression stand gantry 306. Probes 314 and 320 scan breast 162 in the direction of the x-axis in the cranial caudal (CC) view or position. For the medial lateral oblique (MLO) view or position, compression stand gantry 306 is positioned on front of patient 160 next to mammography gantry 309 or on the opposite side. Compression stand gantry 306 includes a pivot mechanism (not shown) such that the angulation of the oblique angle, nominally 45 degrees, may be matched.

Figure 11:
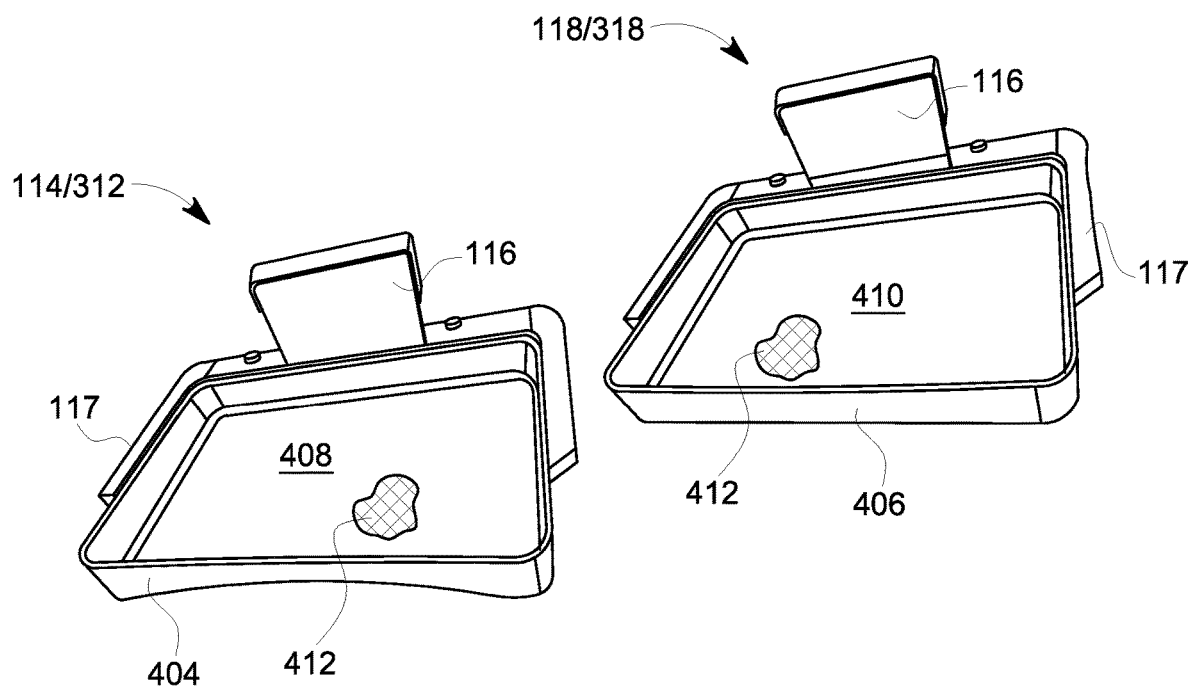
FIG. 11 is a schematic perspective view of an exemplary upper compression paddle and lower compression paddle that may be used with the breast imaging assembly shown in FIGS. 3 and 4.

FIG. 11 is a schematic perspective view of upper (first) compression paddles 114 and 312 and lower (second) compression paddles 118 and 318 that may be used with breast imaging assemblies 100 (shown in FIGS. 3, 4, 6, and 8), 200 (shown in FIG. 9), and 300 (shown in FIG. 10). Upper compression paddles 118 and 318 include a frame 404 and lower compression paddles 118 and 318 include a frame 406, where frame 404 differs from frame 406 in that frame 404 is partially curved and frame 406 is substantially straight, where frame 404 better fits the overall shape of breast 162. Each frame 404 and 406 defines an open region 408 and 410, respectively. Also, each open region 408 and 410 receives a mesh material 412 affixed to frames 404 and 406 to extend over open regions 408 and 410, respectively. Mesh material 412 is deformable relative to frames 404 and 406, thereby facilitating comfort of patient 160 when breast 162 (both shown in FIGS. 8, 9, and 10) is compressed, where mesh material 412 deforms around breast 162 to provide comfortable support. For tomosynthesis imaging, a plastic insert (not shown) may be used in paddle configuration 402 to give a predetermined breast compression if desired. Mesh material 412 has a substantially small attenuation coefficient for x-rays and ultrasound waves.

Figure 12:
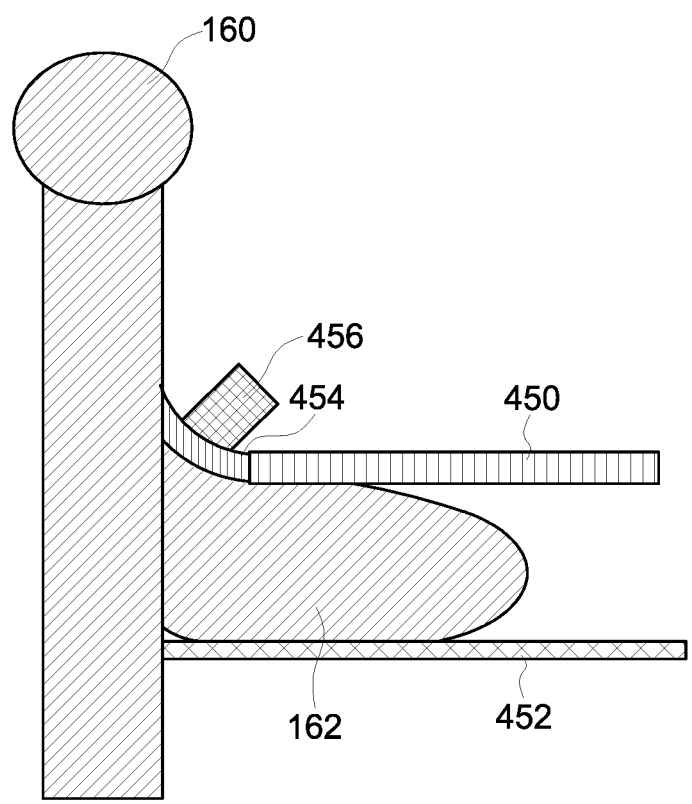
FIG. 12 is a schematic side view of an alternative upper compression paddle and lower compression paddle that may be used with the breast imaging assembly shown in FIGS. 3 and 4.

FIG. 12 is a schematic side view of an alternative upper compression paddle 450 and lower compression paddle 452 that may be used with breast imaging assembly 100 (shown in FIGS. 3 and 4). In this alternative embodiment, upper compression paddle 450 includes a curved section 454 that is shaped to account for the natural curvature of breast 162. Curved section 454 facilitates improved ultrasound scanning of that portion of breast 162 closest to the torso of human patient 160 when breast 162 is compressed between paddles 450 and 452. Such improved ultrasound scanning is facilitated through providing a path of track for an ultrasound probe 456 that captures imaging of approximately 4 millimeters (mm) to approximately 5 mm that may be typically not captured without curved section 454.

Figure 13:
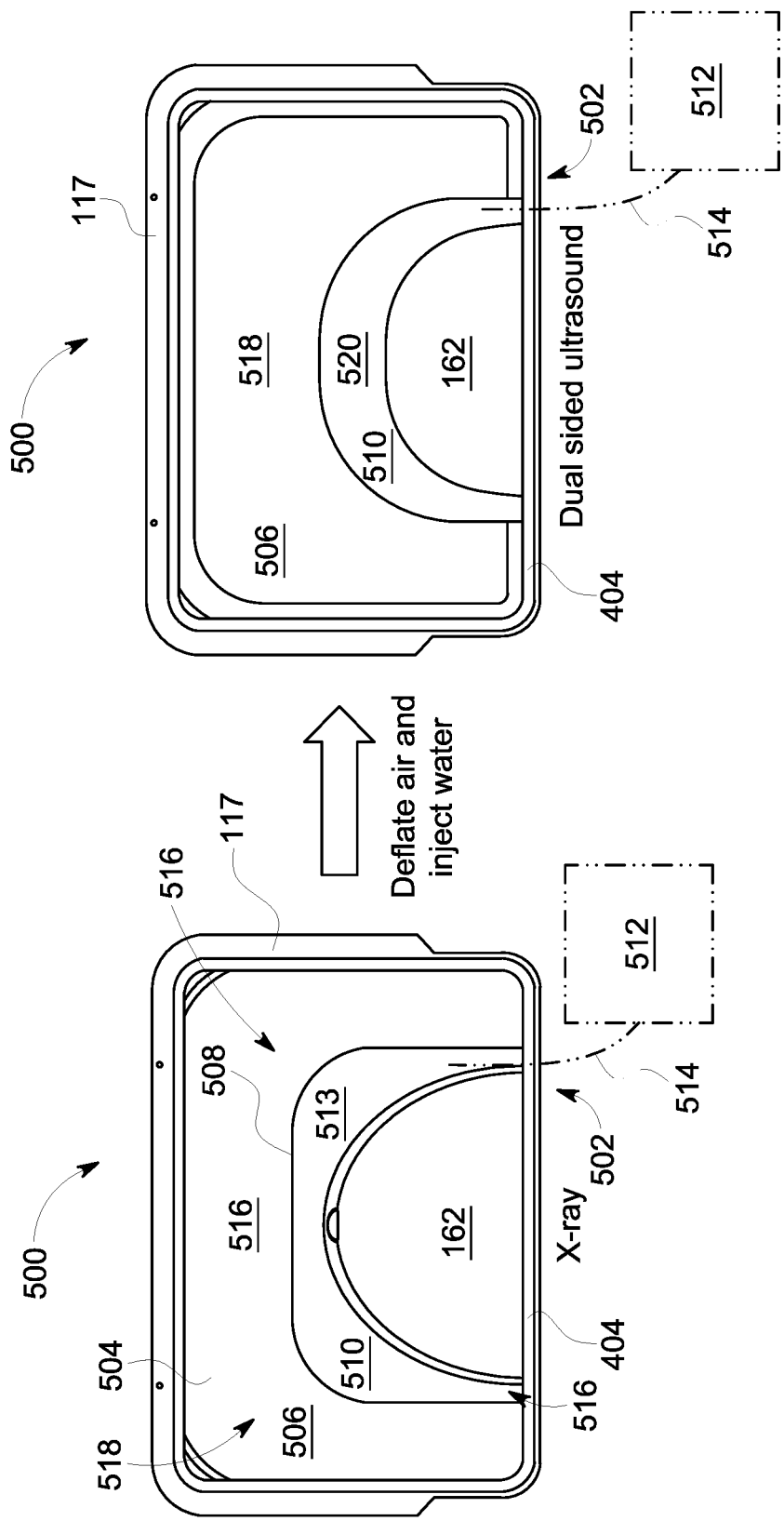
FIG. 13 is a schematic overhead view of an alternative compression paddle including an exemplary ultrasound gel system that may be used with the breast imaging assembly shown in FIGS. 3 and 4.

FIG. 13 is a schematic overhead view of an alternative compression paddle 500 including an exemplary ultrasound gel system 502 that may be used with breast imaging assembly 100 (shown in FIGS. 3 and 4). Upper compression paddles may be similarly configured. In general, one of the issues solved by having a dual sided ultrasound scan is breast contact with the ultrasound waves. For enhanced effectiveness, ultrasound scans typically require a coupling gel between the breast and the transducer for transmission. The coupling gel facilitates transmission of the high-frequency ultrasound waves, since air is a poor transmission medium and boundaries between air and water or tissues reflect most of the wave energy. Even thin layers of air or small bubbles significantly attenuate ultrasound transmission through them.

In the exemplary embodiment, compression paddle 500 includes a fluid-tight containment 504 that defines a fluid chamber 506 therein. Compression paddle 500 also includes ultrasound gel system 502 that includes a gel/water bladder 508 that defines a gel void 510 therein. Gel/water bladder 508 is fabricated of an ultrasound and x-ray transparent material, e.g., and without limitation, urethane. Ultrasound gel system 502 also includes a gel or water source 512 and gel/water bladder 508 is coupled to gel/water source 512 through a gel/water tube 514. During the x-ray portion of the screening, gel/water bladder 508 is filled with air 516 at atmospheric pressure. Fluid chamber 506 is filled with air 516 at or near atmospheric pressure. Once the shift from x-ray scan to ultrasound scan begins, water, or a similar fluid 518 is injected into fluid chamber 506 while air 516 is expelled therefrom and gel/water 520 is injected into gel void 510 while air 513 is vented therefrom. With some breasts, it may be possible to keep air 516 in fluid chamber 506 during the ultrasound study. Once water 518 pressure and gel/water 520 pressure are substantially equalized, sufficient gel/water 520 for ultrasound imaging surrounds breast 162 in compression paddle 500 at least partially due to breast 162 substantially conforming to compression paddle 500 due to gravity and force induced on breast 162 by the other compression paddle (not shown). In contrast, for the other compression paddle, since the tissue rounds on the edges of breast 162, even under compression, a significantly greater amount of gel/water 520 will be necessary. Compression paddle 500 and ultrasound gel system 502 include sufficient fluid transfer devices to inject water and gel into, and vent air from, fluid chamber 506 and gel/water bladder 508 as well as remove water and gel from, and permit air entry into, fluid chamber 506 and gel/water bladder 508.

In this embodiment, gel/water bladder 508 is inflated with air 516 during the x-ray imaging and then filled with ultrasound gel 520 during the ultrasound imaging. This facilitates producing better coupling on the edges of breast 162 without compromising the x-ray or ultrasound image quality. Furthermore it will serve to protect x-ray detector device 108 (shown in FIGS. 3, 4, 8, and 9) from damage by ultrasound gel 520. Inflating gel/water bladder 508 with air 516 during x-ray imaging facilitates more accurate registration of the x-ray and ultrasound images as breast 162 will not move substantially between the two different acquisitions. It may also provide added comfort to human patient 160 (shown in FIGS. 8, 9, and 10) as the compression force will be more uniformly distributed over breast 162 and thus decreasing the pressure on any one area.

Figure 14:
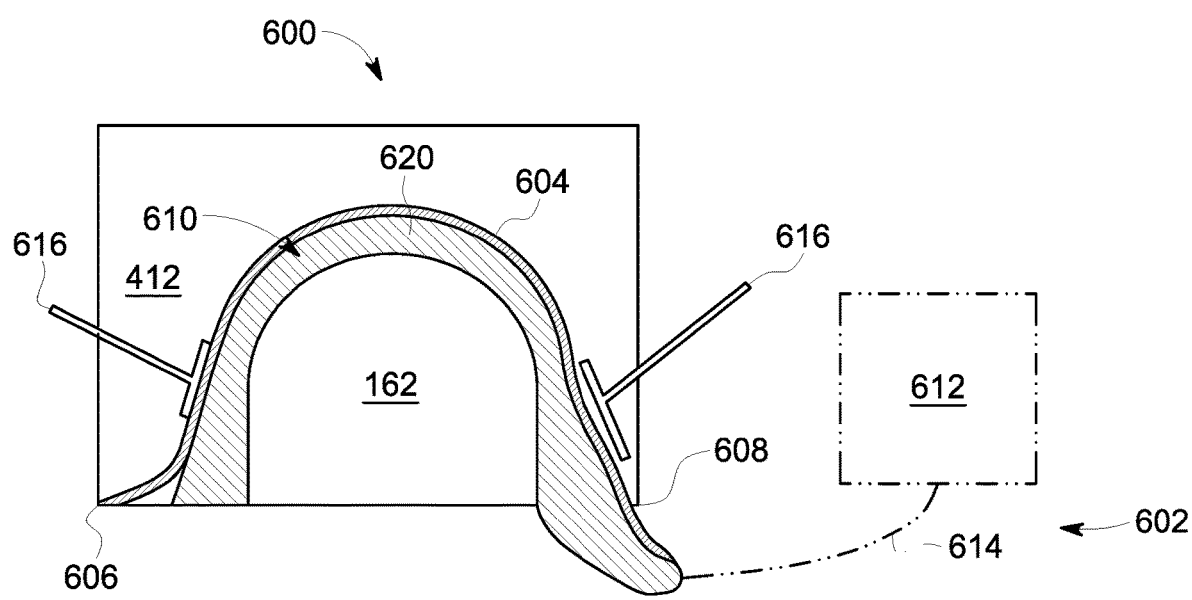
FIG. 14 is a schematic overhead view of another alternative compression paddle including an alternative ultrasound gel and gel dam system that may be used with the breast imaging assembly shown in FIGS. 3 and 4.
Figure 15:
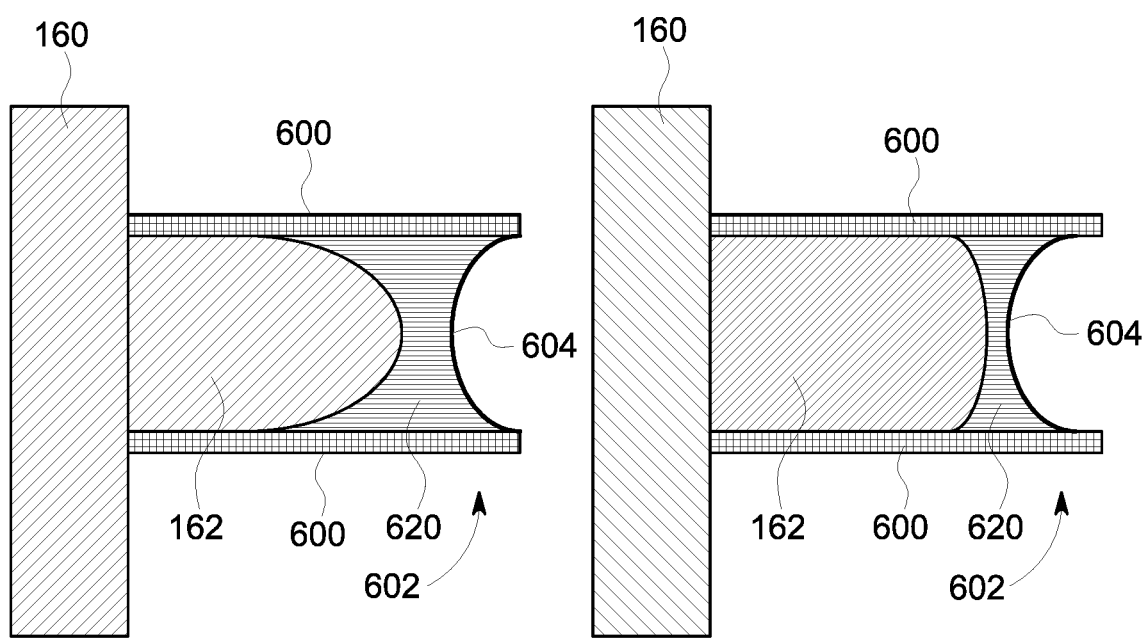
FIG. 15 is a schematic side view of the compression paddle and the alternative ultrasound gel and gel dam system shown in FIG. 14.

FIG. 14 is a schematic overhead view of another alternative compression paddle 600 including an alternative ultrasound gel and gel dam system 602 that may be used with breast imaging assembly 100 (shown in FIGS. 3 and 4). FIG. 15 is a schematic side view of compression paddle 600 and ultrasound gel and gel dam system 602. In this alternative embodiment, compression paddle 600 includes mesh material 412. Compression paddle 600 also includes ultrasound gel system 602 that includes a fabric belt 604 fabricated from a material, e.g., and without limitation, urethane or butyl rubber that may or may not be ultrasound and x-ray transparent. Fabric belt 604 is coupled to corners 606 and 608 of paddle 600. Fabric belt 604 is configured to act as a belt that, after the x-ray, will pull gel 620 around the tissue of breast 162 a small amount to make gel 620 conform to breast 162 such that air gaps are removed and, in some cases, breast 162 is more uniform in thickness. Fabric belt 604 and gel 620 conform to breast 162 and define a void 610 therebetween. Ultrasound gel system 602 also includes a gel source 612 and void 610 is coupled to gel source 612 through a gel tube 614. Some embodiments of ultrasound gel system 602 also include devices such as a plurality of push rods 616 that facilitate the uniformity of gel elimination of air gaps around breast 162 in cooperation with fabric belt 604. Push rods 616 cooperate with gel 620 and fabric belt 604 to facilitate the uniformity of breast 162 and more complete high quality ultrasound images of breast 162. Breast 162 will not move substantially between the two different acquisitions.

During the x-ray portion of the screening, void 610 is filled with air (not shown in FIGS. 14 and 15) at atmospheric pressure. Once the shift from x-ray scan to ultrasound scan begins, gel 620 is injected into void 610 while air is vented therefrom through the mesh paddles and around fabric strap 616. Once sufficient gel 620 for ultrasound imaging surrounds breast 162 at lower compression paddle 600 and as much as possible at the upper compression paddle (not shown), additional gel may be added by hand or by a mound of gel placed in front of the top ultrasound transducer before scanning commences. A dispenser in front of the top ultrasound transducer may be placed in front of the top ultrasound transducer before and during scanning. Lower compression paddle 600 and ultrasound gel system 602 include sufficient fluid transfer devices to inject gel 620 into, and vent air from, paddle 600 as well as remove gel 620 from, and permit air entry into, paddle 600.

Figure 16:
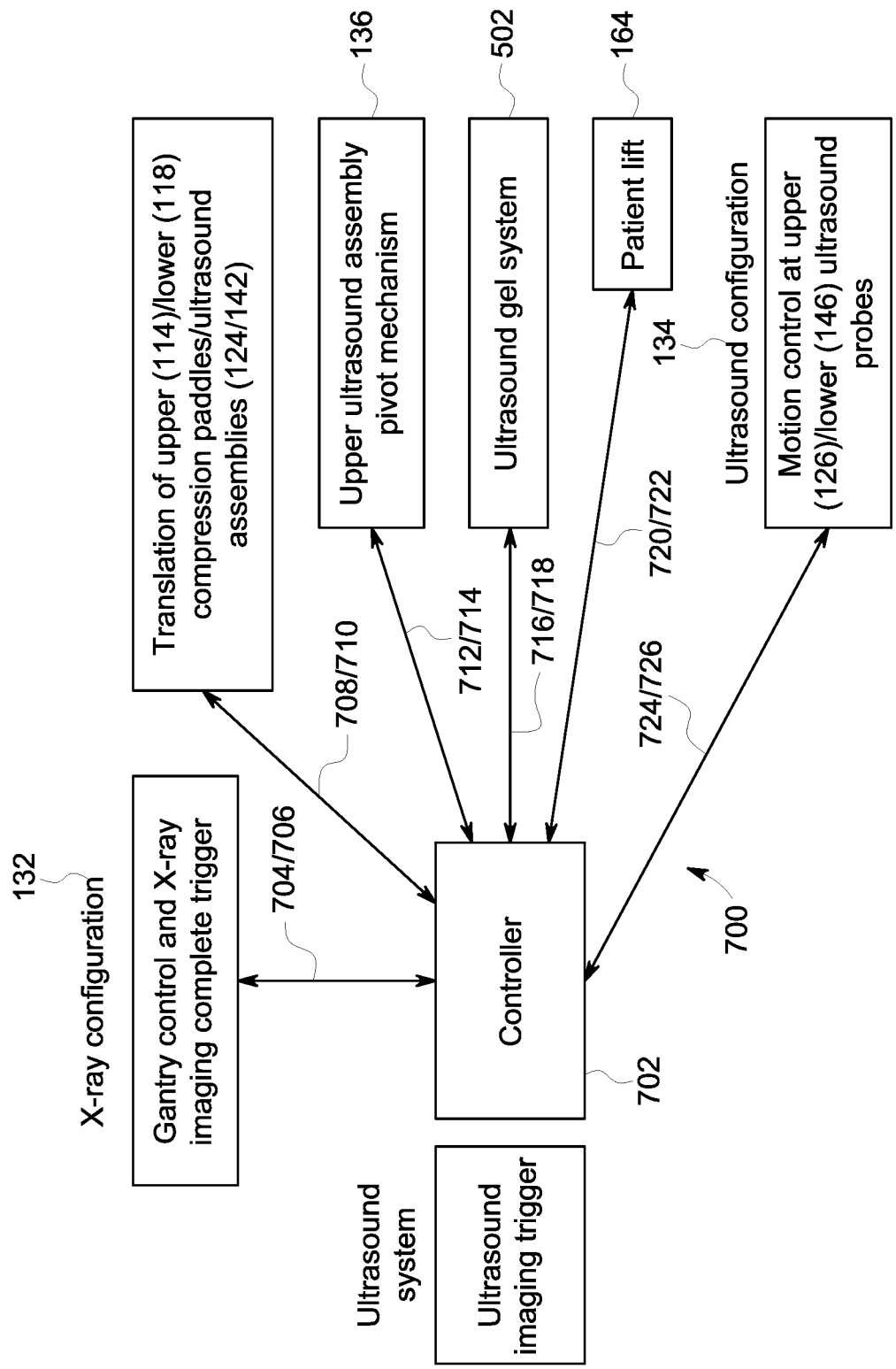
FIG. 16 is a schematic view of an exemplary control system that may be used with the breast imaging assembly shown in FIGS. 3 and 4.

FIG. 16 is a schematic view of an exemplary control system 700 that may be used with breast imaging assembly 100 (shown in FIGS. 3 and 4). Control system 700 includes at least one controller 702. Controller 702 regulates and synchronizes operation of the devises described above to facilitate expedient x-ray and ultrasound scanning and facilitate comfort of human patient 160.

Referencing FIGS. 3, 4, 5, 6, 7, 8, 12, 13, 14, 15, and 16, while breast imaging assembly 100 is in x-ray configuration 132, controller 702 communicates with x-ray system control which controls x-ray source 104 and x-ray detection device 108. Controller 702 transmits command signals 704 to, and receives feedback signals 706 from, the x-ray system control which transmits command signals to x-ray source 104 and detection device 108, and the associated drive and measurement devices thereof.

Also, when breast imaging assembly 100 is shifting from x-ray configuration 132 to ultrasound configuration 134, controller 702 communicates with upper compression paddle 114, lower compression paddle 118, upper ultrasound assembly 124, and lower ultrasound assembly 142. Controller 702 transmits command signals 708 to, and receives feedback signals 710 from, paddles 114 and 118 and assemblies 124 and 142, and the associated drive and measurement devices thereof. Further, controller 702 communicates with pivot mechanism 136, where controller 702 transmits command signals 712 to, and receives feedback signals 714 from, pivot mechanism 136, and the associated drive and measurement devices thereof. Moreover, controller 702 communicates with ultrasound gel system 502, where controller 702 transmits command signals 716 to, and receives feedback signals 718 from, ultrasound gel system 502, and the associated drive and measurement devices thereof. In addition, controller 702 communicates with translatable device 164, where controller 702 transmits command signals 720 to, and receives feedback signals 722 from, translatable device 164, and the associated drive and measurement devices thereof.

Furthermore, when breast imaging assembly 100 is in ultrasound configuration 134, controller 702 communicates with the ultrasound system control which transmits signals to upper ultrasound probe 126 and lower ultrasound probe 146, where ultrasound system controller 702 transmits command signals 724 to, and receives feedback signals 726 from, probes 126 and 146, and the associated drive and measurement devices thereof. In the exemplary embodiment, controller 702 does not control x-ray image acquisition or ultrasound image acquisition. Rather, in contrast, an x-ray system control scheme and an ultrasound system control scheme controls those features. Controller 702 for systems 100 and 200 have a "handshaking" relationship with the x-ray system control scheme and an ultrasound system control scheme. Specifically, controller 702 sends signals to, and receives signals from, the x-ray system control scheme and the ultrasound system control scheme and, optionally, a gantry system control scheme of the x-ray system. The signals from controller 702 are limited to start and stop imaging and movement of gantry 102/202.

Figure 17:
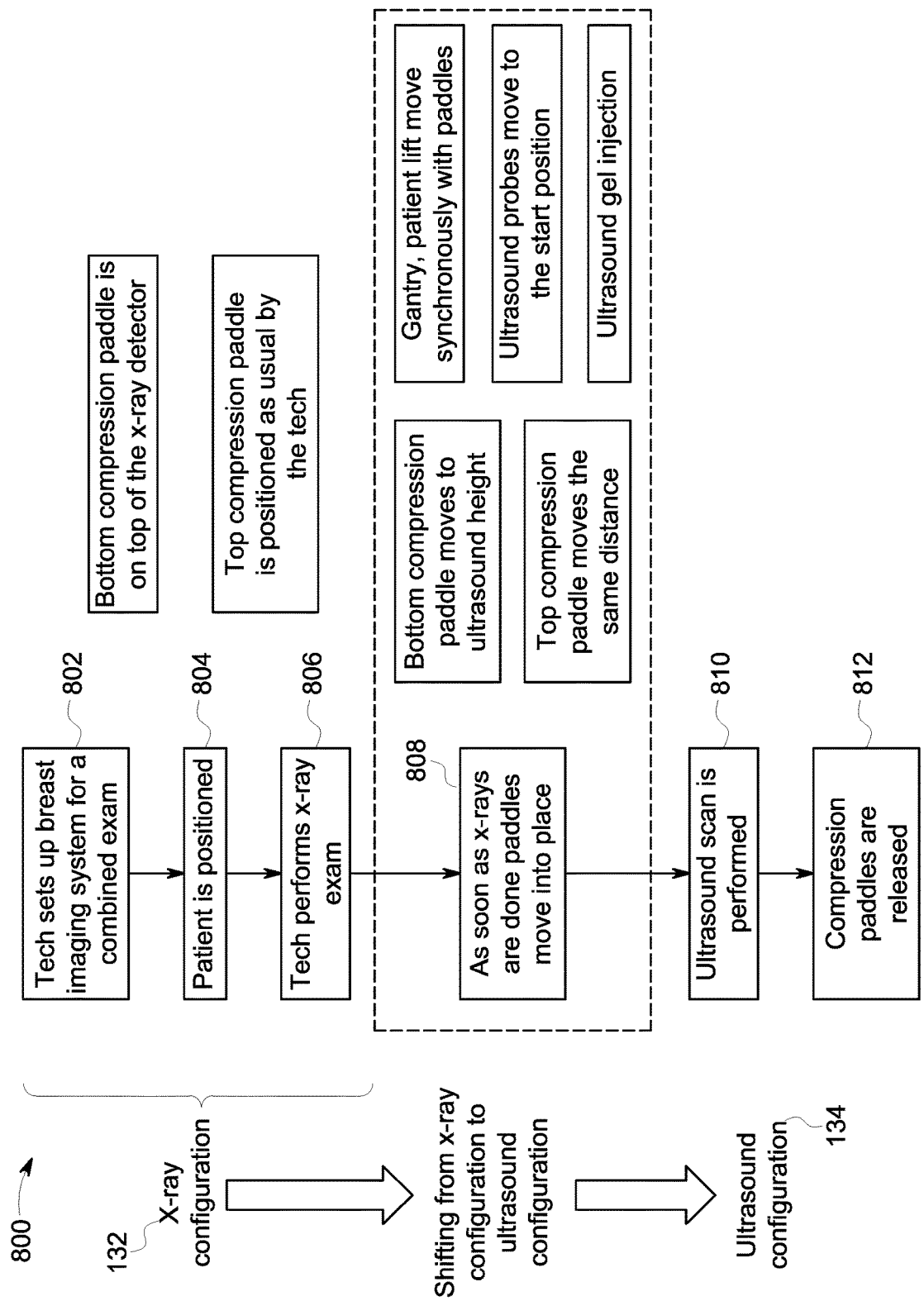
FIG. 17 is an exemplary method of imaging an object through operating the breast imaging assembly shown in FIGS. 3 and 4.

FIG. 17 is an exemplary method 800 of imaging an object through operating breast imaging assembly 100 (shown in FIGS. 3 and 4). Referring to FIGS. 3, 4, 5, 6, 7, 8, 13, 14, 15, 16, and 17, a medical technologist (not shown) sets up 802 breast imaging system 100 for a combined examination including x-ray and ultrasound scanning and imaging. Breast imaging system 100 is initially set up in tomosynthesis x-ray configuration 132 with upper ultrasound assembly 124 in the raised position, upper compression paddle 114 in a raised position above lower compression paddle 118, lower ultrasound probe 146 in the parked position adjacent gantry 102 on first side 150 of lower compression paddle 118, and lower compression paddle 118 with lower ultrasound assembly 142 resting on x-ray detection device 108.

Once breast imaging assembly 100 is set up in mammography x-ray configuration 132, patient 160 is positioned 804 on translatable device 164, i.e., lift and support device 164. Lift and support device 164 is positioned at a height proper for comfortable positioning and compression of breast 162. Breast 162 is positioned within mesh material 412 on lower compression paddle 118 and upper compression paddle 114, also with mesh material 412, is lowered to compress breast 162 and adjusts the x-ray gantry height through the x-ray system control scheme. In some embodiments, the technologist manually adjusts paddles 114 and 118 to properly compress breast 162. In other embodiments, the technologist uses control system 700 and controller 702 to position lift and support device 164 through drive motor command signals 720 and lift and support device position feedback measurement signals 722, and position upper compression paddle 114 through motor command signals 708 and paddle position feedback measurement signals 710. Under some circumstances, lower compression paddle 118, and possible x-ray detection device 108 may also need to be height adjusted. Once human patient 160 is compressed, the technologist uses the x-ray system control scheme to energize x-ray source 104 and transmit x-rays (not shown) through upper paddle 114 (upper ultrasound assembly 124 is pivoted out of the x-ray transmission path), breast 162, and lower paddle 118 to x-ray detection device 108. Mesh material 412 presents a relatively small attenuation of the x-rays. The resultant x-ray image data is collected and stored for subsequent imaging.

Once the x-ray portion of the screening of breast 162 is completed, controller 702 shifts 808 breast imaging assembly 100 from x-ray configuration 132 to ultrasound configuration 134. As breast imaging assembly 100 shifts from mammography configuration 132 to ultrasound configuration 134, upper ultrasound assembly 124 pivots down to the lowered position on top of upper paddle 114 as a function of command signal 712 to the associated drive motor (not shown) and feedback signals 714. If not already there, upper ultrasound probe 126 moves to the ultrasound start position proximate patient 160 as a function of command signal 724 to the associated drive motor (not shown) and feedback signals 726.

Also, as breast imaging assembly 100 shifts from mammography configuration 132 to ultrasound configuration 134, lower ultrasound probe 146 moves from the parked position on first side 150 of lower compression paddle 118 toward second side 152 of lower compression paddle 118 as a function of command signal 724 to the associated drive motor (not shown) and feedback signals 726.

Further, as breast imaging assembly 100 shifts from mammography configuration 132 to ultrasound configuration 134, lower compression paddle 118 with lower ultrasound assembly 142 translates, i.e., raises upward to its ultrasound height from x-ray detection device 108 toward x-ray source 104 substantially synchronously with upper compression paddle 114, also translating to its ultrasound height, as a function of command signal 708 to the associated drive motor (not shown) and feedback signals 710. The range of translating motion is within, and including, approximately 1 cm and 3 cm, with the exemplary embodiment translating approximately 2 cm.

Moreover, as breast imaging assembly 100 shifts from mammography configuration 132 to ultrasound configuration 134, with breast 162 of patient 160 maintained between upper compression paddle 114 and lower compression paddle 118, lift and support device 164 translates synchronously with compression paddles 114 and 118 as a function of command signal 720 to the associated drive motor (not shown) and feedback signals 722. Therefore, breast imaging assembly 100 facilitates execution of both x-ray scans and ultrasound scans while breast 162 remains substantially compressed with a similar compression during both procedures. Some compression relaxation may be performed during the shift from the x-ray scan configuration to the ultrasound scan configuration for the comfort of patient 160.

In addition, during the x-ray portion of the screening, fluid chamber 506 and gel/water bladder 508 are filled with air 516 at atmospheric pressure. As breast imaging assembly 100 shifts from mammography configuration 132 to ultrasound configuration 134, with breast 162 of patient 160 maintained between upper compression paddle 114 and lower compression paddle 118, water 518 is injected into fluid chamber 506 while air 512 is expelled therefrom and gel 520 is injected into gel void 510 while air 512 is vented therefrom as a function of command signal 716 to the associated drive motor(s) (not shown) and feedback signals 718. Once water 518 pressure and gel 520 pressure are substantially equalized, sufficient gel 520 for ultrasound imaging surrounds breast 162 in lower compression paddle 500 at least partially due to breast 162 substantially conforming to lower compression paddle 500 due to gravity and force induced on breast 162 by upper compression paddle 114.

Therefore, in the exemplary embodiment, with breast 162 compressed between compression paddles 114 and 118, the pivoting of upper ultrasound assembly 124, movement of lower ultrasound probe 146, translation of paddles 114 and 118, translation of lift and support device 164, and the introduction of ultrasound gel 520 into gel/water bladder 508 occur substantially simultaneously and synchronously to facilitate decreasing the amount of time human patient 160 must maintain breast 162 between compression paddles 114 and 118 to reduce discomfort. Alternatively, such pivoting, moving, and translating are executed in any sequence that enables operation of breast imaging assembly 100 as described herein.

Once breast imaging assembly 100 completes the shift to ultrasound configuration 134, lower ultrasound probe 146 and upper ultrasound probe 126 scan (sweep) 810 breast 162 substantially simultaneously as a function of command signal 724 to the associated drive motor (not shown) and feedback signals 726 to capture ultrasound data for storage and subsequent imaging. The stored ultrasound image data and the stored x-ray image data are co-registered with standard deformable registration techniques. Once the ultrasound scan is completed, compression paddles 114 and 118 are released 812 as a function of command signals 708 and feedback 710 such that upper compression paddle 114 raises and lower compression paddle 118 returns to the top of x-ray detection device 108 such that patient 160 can withdraw breast 162.

In addition to the devices described above for mammography and ultrasound imaging systems, such imaging systems include additional components known to those skilled in the art and not described herein. Such additional components are not essential for describing the aspects of operation of the imaging systems as described herein, and are therefore excluded.

The above-described breast imaging systems include enhancements to existing x-ray systems to include features that facilitate significant reductions in the shifting of the breast being imaged between the x-ray imaging and ultrasound imaging. Specifically, the breast imaging systems described herein integrate x-ray imaging and ultrasound imaging on the same machine with substantially the same compression induced on the breast being imaged and substantially similar positions for both images. As such, the breast imaging systems described herein are configured such that the detector is movable separate from the compression system such that the compression system and gantry may be moved in a synchronized fashion where the detector is lowered and the patient remains in compression and does not move significantly. Also, as such, the compression system couples to the mammography gantry as an attachment to the compression arm such that the compression system operates separately or in conjunction with the existing mammography compression system. More specifically, the embodiments described herein use two ultrasound probes and scan from the top of the breast and then the bottom of the breast. Such dual-sided ultrasound scanning without interfering with the x-ray imaging detector is facilitated with a mechanism to move the breast upward with the upper and lower ultrasound transducers without hurting the woman while she is compressed. Therefore, the breast can remain in standard mammography configuration in close proximity to the x-ray detector. Once the x-ray portion of the exam is completed, the gantry including the x-ray detector are moved downward slightly and the two compression paddles move together such that the net effect on the breast is that the breast is merely lifted slightly. In addition, if x-ray imaging is performed, the geometry of the breast to detector and tube motion is not altered and no modification of the tomosynthesis reconstruction techniques are required. Once the x-ray portion of the exam is completed, the gantry including the x-ray detector are moved downward slightly and the two compression paddles move together such that the net motion effect on the breast is less than the 3 cm required for the ultrasound probe. In addition, the two compression paddles include a mesh material that contacts the breast to support it without significantly the x-ray or ultrasound transmission and allowing for ultrasound coupling gel to penetrate to the breast. Further, small bladders are integrated into the compression paddles such that when the x-ray image the gantry moves, the paddles move and the little bladder in each paddle fills with ultrasound gel or water such that good contact with the breast for the ultrasound is facilitated. The systems described herein are compatible with existing mammography and tomosynthesis systems and may be installed as a retrofit upgrade without modification to the x-ray system.

An exemplary technical effect of the methods, systems, and apparatus described herein includes at least one of: (a) facilitate integration of x-ray breast imaging systems with ultrasound imaging systems; (b) facilitate significant reductions in repositioning of a woman's breast for an ultrasound exam after an x-ray scan; (c) automatically inject ultrasound gel into a bladder within the upper and lower ultrasound paddles to improve ultrasound probe contact with the breast; (d) using a mesh on each of the lower and upper ultrasound paddles to allow for ultrasound coupling gel to make contact with both the ultrasound probe and the patient skin; (e) reducing a number of patient visits for breast cancer screening exams; (f) reducing the time required to acquire and analyze results of integrated x-ray and ultrasound exams; (g) reducing cost and length of time for an ultrasound scan; (h) reducing errors associated with repositioning the patient; (i) improving co-registration of x-ray and ultrasound images with standard deformable registration techniques, thereby improving diagnoses and/or reducing time and skill required by a medical professional for analysis of acquired images; (j) improving diagnosis of dense breasts; (k) reducing costs for a combination ultrasound/x-ray imaging mammographic examination system; (l) providing a field-upgradable system for existing mammography and mammography systems; (m) generating ultrasound waves that penetrate from two directions, thereby facilitating imaging the entire breast; (n) configuring breast imaging systems such that the detector is movable separate from the compression system and such that the compression system and gantry may be moved in a synchronized fashion where the detector is lowered and the patient remains in compression and does not move significantly; and (o) coupling the compression system to the mammography gantry as an attachment to the compression arm such that the compression system operates separately or in conjunction with the existing mammography compression system.

Exemplary embodiments of breast imaging systems, and methods of operating such systems and devices are not limited to the specific embodiments described herein, but rather, components of systems and/or steps of the methods may be utilized independently and separately from other components and/or steps described herein. For example, the methods may also be used in combination with other systems requiring sequential imaging and the associated methods, and are not limited to practice with only the breast imaging system and methods as described herein. Rather, the exemplary embodiment can be implemented and utilized in connection with many other sequential imaging applications.

Although specific features of various embodiments of the disclosure may be shown in some drawings and not in others, this is for convenience only. In accordance with the principles of the disclosure, any feature of a drawing may be referenced and/or claimed in combination with any feature of any other drawing.

Some embodiments involve the use of one or more electronic or computing devices. Such devices typically include a processor, processing device, or controller, such as a general purpose central processing unit (CPU), a graphics processing unit (GPU), a microcontroller, a reduced instruction set computer (RISC) processor, an application specific integrated circuit (ASIC), a programmable logic circuit (PLC), a field programmable gate array (FPGA), a digital signal processing (DSP) device, and/or any other circuit or processing device capable of executing the functions described herein. The methods described herein may be encoded as executable instructions embodied in a computer readable medium, including, without limitation, a storage device and/or a memory device. Such instructions, when executed by a processing device, cause the processing device to perform at least a portion of the methods described herein. The above examples are exemplary only, and thus are not intended to limit in any way the definition and/or meaning of the term processor and processing device.

This written description uses examples to disclose the embodiments, including the best mode, and also to enable any person skilled in the art to practice the embodiments, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An imaging assembly comprising:
   a gantry;
   a compression system configured to receive and compress an object to be imaged, said compression system comprising:
   a first compression paddle coupled to said gantry; and
   a second compression paddle coupled to said gantry;
   an x-ray source;
   an x-ray detection device coupled to said gantry, said detection device proximate said second compression paddle; and
   an ultrasound system comprising:
   a first ultrasound probe coupled to said first compression paddle, said first ultrasound probe configured to acquire a first portion of the ultrasound image information of the object to be imaged; and
   a second ultrasound probe coupled to said second compression paddle, said second ultrasound probe configured to acquire a second portion of the ultrasound image information of the object to be imaged
   wherein said first ultrasound probe is configured to be positioned between said x-ray source and said x-ray detector, said first ultrasound probe is configured to pivot from a first position extending over at least a portion of said first compression paddle to a second position proximate said gantry, wherein, in the second position, said first ultrasound probe is substantially removed from an x-ray beam emanated from said x-ray source toward said x-ray detection device;
   wherein said first ultrasound probe is further configured to pivot from the second position to the first position to facilitate acquisition of the first portion of the ultrasound image information of the object to be imaged.

2. The imaging assembly in accordance with claim 1, wherein said gantry is configured to translate in a direction opposite to said second compression paddle such that a predetermined distance between said x-ray detection device and said second compression paddle is established.

3. The imaging assembly in accordance with claim 1, wherein said x-ray detection device is substantially stationary with respect to said gantry and said second compression paddle is configured to translate in a direction defined between said x-ray detection device and said first ultrasound probe.

4. The imaging assembly in accordance with claim 3, wherein said first compression paddle is configured to translate substantially synchronously with said second compression paddle in the direction defined between said x-ray detection device and said first ultrasound probe with the object to be imaged remaining compressed between the first compression paddle and the second compression paddle.

5. The imaging assembly in accordance with claim 3 further comprising a translatable device configured to translate substantially synchronously with said first compression paddle and said second compression paddle in the direction defined between said x-ray detection device and said first ultrasound probe.

6. The imaging assembly in accordance with claim 5, wherein the object to be imaged is a human breast and said translatable device is a lift and support device configured to hold a human patient.

7. The imaging assembly in accordance with claim 5, wherein at least one of said first compression paddle and said second compression paddle comprises a bladder coupled to an ultrasound gel source, said bladder configured to extend about at least a portion of the object to be imaged, said bladder further configured to receive ultrasound gel from said ultrasound gel source and facilitate contact of the ultrasound gel with the object to be imaged.

8. The imaging assembly in accordance with claim 7 further comprising at least one controller configured to synchronize translation of said gantry, said first compression paddle, said second compression paddle, and said translatable device and transfer of the ultrasound gel from said ultrasound gel source to said bladder.

9. The imaging assembly in accordance with claim 1, wherein said second compression paddle comprises a first side proximate said gantry and a second side opposite said first side, said second ultrasound probe parked proximate said first side when said x-ray source emanates the x-ray beam toward said x-ray detection device.

10. The imaging assembly in accordance with claim 9, wherein said first ultrasound probe and second ultrasound probe are configured to move substantially synchronously to acquire the first portion and the second portion of the ultrasound image information of the object to be imaged substantially simultaneously.

11. The imaging assembly in accordance with claim 10 further comprising at least one controller configured to synchronize movement of said first ultrasound probe and said second ultrasound probe.

12. The imaging assembly in accordance with claim 1, wherein said first compression paddle and said second compression paddle each comprise a frame defining an open region and a mesh material affixed to said frame over the open region, wherein said mesh material is deformable relative to said frame.

13. A retrofit upgrade package for an installed legacy imaging system, said retrofit upgrade package comprising:
   a compression system configured to receive and compress an object to be imaged, said compression system comprising:
   a first compression paddle configured to be coupled to a gantry; and
   a second compression paddle configured to be coupled to the gantry; and an ultrasound system comprising:
    a first ultrasound probe mounted on said first compression paddle, said first ultrasound probe configured to acquire a first portion of ultrasound image information of the object to be imaged; and
    a second ultrasound probe coupled to said second compression paddle, said second ultrasound probe configured to acquire a second portion of the ultrasound image information of the object to be imaged
  wherein said first ultrasound probe is configured to be positioned between an x-ray source and an x-ray detector, said first ultrasound probe is configured to pivot from a first position extending over at least a portion of said first compression paddle to a second position proximate the gantry, wherein, in the second position, said ultrasound probe is substantially removed from an x-ray beam emanated from the x-ray source toward the x-ray detection device; and
  wherein said first ultrasound probe is further configured to pivot from the second position to the first position to facilitate acquisition of the first portion of the ultrasound image information of the object to be imaged.

14. The retrofit upgrade package in accordance with claim 13 further comprising a translatable device configured to translate substantially synchronously with said first compression paddle and said second compression paddle.

15. The retrofit upgrade package in accordance with claim 13, wherein at least one of said first compression paddle and said second compression paddle comprises a bladder coupled to an ultrasound gel source, said bladder configured to extend about at least a portion of the object to be imaged, said bladder further configured to receive ultrasound gel from said ultrasound gel source and facilitate contact of the ultrasound gel with the object to be imaged.

16. The retrofit upgrade package in accordance with claim 13, wherein said second compression paddle comprises a first side proximate the gantry and a second side opposite said first side, said second ultrasound probe parked proximate said first side when the x-ray source emanates an x-ray beam toward the x-ray detection device.

17. The retrofit upgrade package in accordance with claim 13, wherein said first ultrasound probe and second ultrasound probe are configured to move substantially synchronously to acquire the first portion and the second portion of the ultrasound image information of the object to be imaged substantially simultaneously.

18. The retrofit upgrade package in accordance with claim 13, wherein said first compression paddle and said second compression paddle each comprise a frame defining an open region and a mesh material affixed to said frame over the open region, wherein said mesh material is deformable relative to said frame.

19. A method of imaging an object, said method comprising:
  positioning a first compression paddle to receive an object to be imaged;
  positioning a second compression paddle to extend over at least a portion of an x-ray detector;
  positioning the object to be imaged between the first compression paddle and the second compression paddle;
  generating x-ray image data of the object to be imaged;
  after generating the x-ray image data and prior to generating ultrasound image data, translating the first compression paddle and the second compression paddle substantially synchronously with the object to be imaged remaining therebetween; and
  moving a first ultrasound probe across the first compression paddle and moving a second ultrasound probe across the second compression paddle substantially simultaneously to generate ultrasound image data.

20. The method in accordance with claim 19, wherein translating the first compression paddle comprises pivoting the first ultrasound probe from a first position extending substantially vertically to a second position extending substantially horizontally over at least a portion of the first compression paddle.

21. The method in accordance with claim 19, wherein moving the first compression paddle and the second compression paddle comprises translating the second compression paddle upward and away from the x-ray detector.

22. The method in accordance with claim 21 further comprising translating a translatable device including a breast examination patient upward substantially synchronously with the first compression paddle and the second compression paddle.

23. The method in accordance with claim 19 further comprising translating the x-ray detector downward and away from the second compression paddle.

24. The method in accordance with claim 19, wherein positioning a second compression paddle to extend over at least a portion of an x-ray detector comprises moving the second ultrasound probe to a parked position to substantially reduce interference with generating x-ray image data.

25. The method in accordance with claim 19, wherein translating the first compression paddle and the second compression paddle comprises transferring ultrasound gel from an ultrasound gel source to a bladder within at least one of the first compression paddle and the second compression paddle substantially synchronously with translating the first compression paddle and the second compression paddle.

* * * * *